(12) United States Patent
Jain et al.

(10) Patent No.: US 7,183,445 B2
(45) Date of Patent: Feb. 27, 2007

(54) CYCLOHEXYL DERIVATIVES AS SELECTIVE ESTROGEN RECEPTOR MODULATORS

(75) Inventors: Nareshkumar F. Jain, Raritan, NJ (US); Mark J. Macielag, Raritan, NJ (US); William V. Murray, Raritan, NJ (US); Raymond A. Ng, Raritan, NJ (US); Zhihua Sui, Raritan, NJ (US)

(73) Assignee: Janssen Pharmaceutica N.V (BE)

( * ) Notice: Subject to any disclaimer, the term of this patent is extended or adjusted under 35 U.S.C. 154(b) by 128 days.

(21) Appl. No.: 10/858,435

(22) Filed: Jun. 1, 2004

(65) Prior Publication Data

US 2005/0009799 A1 Jan. 13, 2005

(51) Int. Cl.
*C07C 39/06* (2006.01)
*C07C 39/23* (2006.01)
*C07D 295/027* (2006.01)
*C07D 265/30* (2006.01)

(52) U.S. Cl. .................. 568/707; 568/707; 568/425; 568/585; 546/238; 544/106

(58) Field of Classification Search .............. 568/707, 568/425, 585; 546/238; 544/106
See application file for complete search history.

(56) References Cited

U.S. PATENT DOCUMENTS

| | | | |
|---|---|---|---|
| 4,190,433 A | 2/1980 | Laanio et al. | |
| 4,229,207 A | 10/1980 | Laanio et al. | |
| 4,340,415 A | 7/1982 | Laanio et al. | |
| 4,340,747 A | 7/1982 | Laanio et al. | |
| 6,166,075 A | 12/2000 | Klar et al. | |
| 6,288,126 B1 * | 9/2001 | Lesuisse et al. | 514/681 |

FOREIGN PATENT DOCUMENTS

| | | |
|---|---|---|
| JP | 162665 | 7/1988 |
| WO | WO 99/64393 A1 | 12/1999 |
| WO | WO 00/55137 A1 | 9/2000 |

OTHER PUBLICATIONS

Venkatesan et al., N-Hydroxy-2-(alkyl, aryl or hereroaryl sulfany as matrix metalloproteinase inhibitors, CA 129:230639.*
Levin et al., The preparation and use of ortho-sulfonamido aryl hydroxamic acis as metalloproteinase and TACE inhibitors, CA 128:308308.*
Exhibit A, Search Results.*
Essawy et al., Behavior of a Naphthopyranone Derivative Towards Some Nitrogen and Carbon Nucleophiles, Indian Journal of Chemistry, Section B: Organic 31B(1): 39-43 (1992).*
PCT Search Report, PCT/US04/017362, Dec. 22, 2004.
Baldwin, Jack E., "Rules for Ring Closure: Application to Intramolecular Aldol Condensations in Polyketonic Substrates", Tetrahadron vol. 38, No. 19,pp. 2939-2947, 1982.
Corey, E.J., et al. "New Annulation Processes for Fused and Spiro Rings Based on the Chemistry of Benzothiazoles", Tetrahedron Letters No. 1, (1978) pp. 13-16.
Hamon, David P.G., et al. "An Investigative Study of Kinetic Resolutions by the Sharpless Asysmmetric Dihydroxylation Reaction", Tetrahedron Letters, 57 (2001) 9499-9508.
Zhenfeng, XI, et al., "Copper(I)catalyzed Tandem Inter-Intramolecular Cyclization Reactions of Zirconacycles: Formation of Highly Substiturted Styrenes, Vinylcyclohexadienes, and Related Compounds", Tetrahedron 58 (2002) 117-1117.

* cited by examiner

*Primary Examiner*—Celia Chang
*Assistant Examiner*—R. James Balls

(57) ABSTRACT

The present invention is directed to novel cyclohexyl derivatives, pharmaceutical compositions containing them and their use in the treatment of disorders and diseases mediated by an estrogen receptor.

4 Claims, No Drawings

CYCLOHEXYL DERIVATIVES AS SELECTIVE ESTROGEN RECEPTOR MODULATORS

FIELD OF THE INVENTION

The present invention is directed to novel cyclohexyl derivatives, pharmaceutical compositions containing them and their use in the treatment or prevention of disorders and diseases mediated by an estrogen receptor such as hot flashes, vaginal dryness, osteopenia, osteoporosis, hyperlipidemia, loss of cognitive function, degenerative brain diseases, cardiovascular, cerebrovascular diseases, hormone sensitive cancers and hyperplasia (in tissues including breast, endometrium, and cervix in women and prostate in men), endometriosis, uterine fibroids, osteoarthritis; and as contraceptive agents either alone or in combination with a progestogen or progestogen antagonist. The compounds of the invention are selective estrogen receptor modulators.

BACKGROUND OF THE INVENTION

Estrogens are a group of female hormones essential for the reproductive process and for the development of the uterus, breasts, and other physical changes associated with puberty. Estrogens have an effect on various tissues throughout a woman's body, not only those involved in the reproductive process, such as the uterus, breasts, and external genitalia, but also tissues in the central nervous system, bones, the liver, skin, and the urinary tract. The ovaries produce most of the estrogens in women's body.

Menopause is defined as the permanent cessation of menses due to loss of ovarian follicular function and the almost termination of estrogen production. The midlife transition of menopause is characterized by a decrease in estrogen that provokes both short-term and long-term symptoms with the vasomotor, urogenital, cardiovascular, skeletal and centra nervous systems, such as hot flushes, urogenital atrophy, increased risk of cardiovascular disease, osteoporosis, cognitive and psychological impairment, including an increased risk of cognitive disorders and Alzheimer's disease (AD).

Seventy-five percent of all women experience some occurrence of vasomotor symptoms associated with the onset of menopause such as body sweating and hot flushes. These complaints may begin several years before menopause and in some women may continue for more than 10 years either relatively constant, or as instant attacks without a definable, provoking cause.

Urogenital symptoms associated with the onset of menopause involving the vagina include a sensation of dryness, burning, itching, pain during intercourse, superficial bleeding and discharge, along with atrophy, stenosis. Symptoms involving the urinary tract include a burning sensation during urination, frequent urgency, recurrent urinary tract infections, and urinary incontinence. These symptoms have been reported to occur in up to 50% of all women near the time of menopause and are more frequent a few years after menopause. If left un-treated, the problems can become permanent.

Heart attack and stroke are major causes of morbidity and mortality among senior women. Female morbidity from these diseases increases rapidly after menopause. Women who undergo premature menopause are at greater coronary risk than menstruating women of similar age. The presence of serum estrogen has a positive effect on serum lipids. The hormone promotes vasodilation of blood vessels, and enhances the formation of new blood vessels. Thus the decrease in serum estrogen levels in postmenopausal women results in adverse cardiovascular effect. Additionally, it is theorized that differences in the ability of blood to coagulate may account for the observed difference in the occurrence of heart disease before and after menopause.

The skeleton is under a continuous process of bone degeneration and regeneration in a carefully regulated interaction among the bone cells. These cells are directly affected by estrogen. Estrogen deficiency results in a loss of bone structure, and decrease of bone strength. Rapid loss of bone mass during the year immediately following menopause leads postmenopausal osteoporosis and increased risk of fracture.

Estrogen deficiency is also one of the causes for the degenerative changes in the central nervous system and may lead to Alzheimer's disease and decline of cognition. Recent evidence suggests an association between estrogen, menopause, and cognition. More particularly, it has been reported that estrogen replacement therapy and the use of estrogen in women may prevent the development of AD, and improve cognitive function.

Hormone replacement therapy (HRT)—more specifically estrogen replacement therapy (ERT)—is commonly prescribed to address the medical problems associated with menopause, and also to help hinder osteoporosis and primary cardiovascular complications (such as coronary artery disease) in both a preventive and therapeutical manner. As such, HRT is considered a medical therapy for prolonging the average life span of postmenopausal women and providing a better quality of life.

ERT effectively relieves the climacteric symptoms and urogenital symptoms and has shown significant benefits in the prevention and treatment of heart disease in postmenopausal women. Clinical reports have shown that ERT lowered heart attack rates and mortality rates in populations that received ERT versus similar populations not on ERT. ERT initiated soon after menopause may also help maintain bone mass for several years. Controlled investigations have shown that treatment with ERT has a positive effect even in older women up to age of 75 years.

However, there are numerous undesirable effects associated with ERT that reduce patient compliance. Venous thromboembolism, gallbladder disease, resumption of menses, mastodynia, and a possible increased risk of developing uterine and/or breast cancer are the risks associated with ERT. Up to 30% of women who were prescribed with ERT do not fill the prescription, and the discontinuation rate is between 38% and 70%, with safety concerns, and adverse effects (bloating and break-through bleeding) the most important reasons for discontinuation.

A new class of pharmacological agents known as Selective Estrogen Receptor Modulators or SERMs have been designed and developed as alternatives for HRT. Raloxifene, a nonsteroidal benzothiophere SERM is marketed in the US and Europe for the prevention and treatment of osteoporosis under the trademark of Evista®. Raloxifene has been shown to reduce bone loss and prevent fracture without adversely stimulating endometrial and mammary tissue, though raloxifene is somewhat less efficacious than ERT for protecting against bone loss. Raloxifene is unique and differs significantly from ERT in that it does not stimulate the endometrium and has the potential for preventing breast cancer. Raloxifene has also demonstrated beneficial estrogen agonist effects on cardiovascular risk factors, more specifically through a rapid and sustained decrease in total and low-density lipoprotein cholesterol levels in patients treated with raloxifene. In addition, raloxifene has been shown to reduce plasma concentration of homocysteine, an independent risk factor for atherosclerosis and thromboembolic disease.

However, raloxifene has been reported to exacerbate symptoms associated with menopause such as hot flushes and vaginal dryness, and does not improve cognitive function in senior patients. Patients taking raloxifene have reported higher rates of hot flashes compared with either placebo or ERT users and more leg cramps than placebo users, although women who took ERT had a higher incidence of vaginal bleeding and breast discomfort than raloxifene or placebo users.

As yet, neither raloxifene nor any of the other currently available SERM compounds has been shown to have the ability to provide all the benefits of currently available ERT such as controlling postmenopausal syndrome and preventing AD, without causing adverse side effects such as increasing risk of endometrial and breast cancer and bleeding. Thus there exists a need for compounds which are selective estrogen receptor modulators and which provide all of the benefits of ERT while also addressing the vasomotor, urogenital and cognitive disorders or conditions associated with the decrease in systemic estrogen associated with menopause.

SUMMARY OF THE INVENTION

The present invention is directed to a compound of the general formula (I)

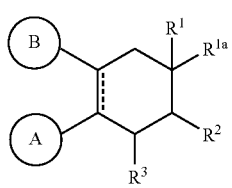

(I)

wherein

----- represents a single or a double bond;

$R^{1a}$ is selected from the group consisting of hydrogen and lower alkyl;

$R^1$ is selected from the group consisting of alkyl, hydroxy substituted alkyl, alkenyl, hydroxy substituted alkenyl, alkynyl, hydroxy substituted alkynyl, alkoxyalkyl, alkoxy-carbonyl, alkyl-carbonyl, aryl-carbonyl, heteroaryl-carbonyl, heterocycloalkyl-carbonyl, alkyl-carbonyl-alkyl, $NR^AR^B$-carbonyl and $NR^AR^B$-alkoxy-alkyl;

$R^A$ and $R^B$ are each independently selected from the group consisting of hydrogen and alkyl; alternatively $R^A$ and $R^B$ are taken together with the N atom to which they are bound to form a heteroaryl or heterocycloalkyl group;

$R^2$ is selected from the group consisting of hydrogen, carboxy, alkyl, hydroxy substituted alkyl, alkenyl, hydroxy substituted alkenyl, alkynyl, hydroxy substituted alkynyl, alkoxyalkyl, alkoxy-carbonyl, alkyl-carbonyl, aryl-carbonyl, heteroaryl-carbonyl, heterocycloalkyl-carbonyl, alkyl-carbonyl-alkyl, $NR^AR^B$-carbonyl and $NR^AR^B$-alkoxy-alkyl;

alternatively $R^1$ and $R^2$ are taken together with the atoms to which they are bound to form a five to eight membered saturated ring structure of the formula

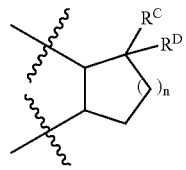

wherein n is an integer from 1 to 4;

wherein $R^C$ and $R^D$ are independently selected from hydrogen, hydroxy, alkyl, alkenyl, alkynyl or alkoxy; alternatively $R^C$ and $R^D$ are taken together with the carbon atom to which they are bound to form an oxo group;

alternatively still, $R^1$ and $R^2$ are taken together with the atoms to which they are bound to form a heteroatom containing saturated ring structure of the formula

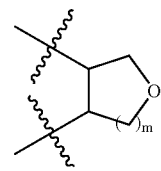

wherein m is an integer from 1 to 3;

$R^3$ is selected from the group consisting of hydrogen and alkyl;

Ⓐ is selected from the group consisting of aryl, aralkyl and heteroaryl; wherein the heteroaryl group is bound to the core structure through a carbon atom; and wherein the aryl, aralkyl or heteroaryl group is optionally substituted with one or more substitutents independently selected from hydroxy, alkoxy, aralkyl, aralkyloxy or $NR^AR^B$-alkoxy;

Ⓑ is selected from the group consisting of aryl, aralkyl and heteroaryl; wherein the heteroaryl group is bound to the core structure through a carbon atom; and wherein the aryl, aralkyl or heteroaryl group is optionally substituted with one or more substitutents independently selected from hydroxy, alkoxy, aralkyl, aralkyloxy or $NR^AR^B$-alkoxy;

provided that when

is a double bond, $R^{1a}$ is hydrogen, $R^2$ is hydrogen, $R^3$ is hydrogen, and Ⓐ and Ⓑ are the same and selected from the group consisting of phenyl or substituted phenyl, wherein the substituents on the phenyl are one to two selected from alkoxy, then $R^1$ is other than hydroxy substituted lower alkyl or alkoxycarbonyl;

provided further that when

is a double bond, $R^{1a}$ is hydrogen or lower alkyl, Ⓐ is phenyl and Ⓑ is phenyl, then $R^1$ is selected from the group consisting of $NR^AR^B$-carbonyl and $NR^AR^B$-alkoxy-alkyl;

provided further that when

----- is a single bond, $R^{1a}$ is hydrogen, $R^2$ is hydrogen or lower alkyl, $R^3$ is hydrogen, and Ⓐ and Ⓑ are the same and are phenyl, then $R^1$ is other than lower alkyl, hydroxy substituted lower alkyl, alkylcarbonyl or alkoxycarbonyl;

provided further that when

----- is a single bond, $R^1$ is lower alkyl, $R^{1a}$ is hydrogen, $R^2$ is hydrogen, $R^3$ is hydrogen and Ⓐ is phenyl, then Ⓑ is other than benzimidazolyl;

provided further that when

----- is a single or double bond, $R^{1a}$ is lower alkyl, $R^3$ is hydrogen, $R^1$ and $R^2$ are taken together with the atoms to which they are bound to form cyclohexyl or 3-hydroxyphenyl and Ⓐ is 4-hydroxyphenyl, then Ⓑ is other than 4-($NR^AR^B$-lower alkoxy)-phenyl, wherein $R^A$ and $R^B$ are each independently selected from hydrogen or lower alkyl or $R^A$ and $R^B$ are taken together with the N atom to which they are bound to form piperidinyl;

provided further than when -----is a single or double bond, $R^{1a}$ is hydrogen, $R^3$ is hydrogen and $R^1$ and $R^2$ are taken together with the atoms to which they are bound to form

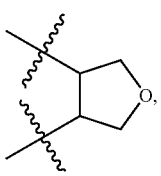

then Ⓐ and Ⓑ are not the same and phenyl;

provided further that when -----is a double bond, $R^{1a}$ is lower alkyl, $R^3$ is hydrogen and $R^1$ and $R^2$ are taken together with the atoms to which they are bound to form a five membered saturated ring structure of the formula

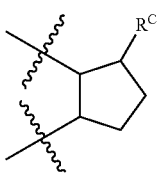

wherein $R^C$ is selected from hydroxy or alkoxy, then Ⓐ and Ⓑ are other than phenyl or substituted phenyl, wherein the substituents on the phenyl are one or more independently selected from hydroxy, alkoxy, aralkyl, aralkyloxy or $NR^AR^B$-alkoxy;

or a pharmaceutically acceptable salt thereof.

The present invention is further directed to compounds of formula (II)

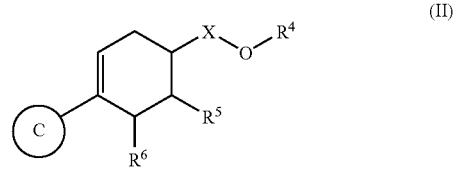

wherein

X is selected from the group consisting C(O) and $CH_2$;

$R^4$ is selected from the group consisting of hydrogen and lower alkyl;

$R^5$ is selected from the group consisting of alkyl;

$R^6$ is selected from the group consisting of -(aralkyl)-Q-(alkyl)-$NR^AR^B$;

Q is selected from the group consisting of O and S;

$R^A$ and $R^B$ are each independently selected from the group consisting of hydrogen and alkyl; alternatively $R^A$ and $R^B$ are taken together with the N atom to which they are bound to form a heteroaryl or heterocycloalkyl group;

Ⓒ is selected from the group consisting of aryl, aralkyl, heteroaryl and heterocycloalkyl; wherein the heteroaryl or heterocycloalkyl group is bound to the core structure through a carbon atom; and wherein the aryl, aralkyl, heteroaryl or heterocycloalkyl group is optionally substituted with one or more substitutents independently selected from halogen, hydroxy, alkoxy, aralkyloxy or $NR^AR^B$-alkoxy;

or a pharmaceutically acceptable salt thereof.

The present invention is further directed to a compound of formula (III)

$$\text{(III)}$$

represents a single or a double bond;

X is selected from the group consisting of C(O) and $CH_2$;

$R^4$ is selected from the group consisting of hydrogen and lower alkyl;

$R^5$ is selected from the group consisting of alkyl;

$R^6$ is selected from the group consisting of -(aralkyl)-Q-(alkyl)-$NR^AR^B$;

Q is selected from the group consisting of O and S;

$R^A$ and $R^B$ are each independently selected from the group consisting of hydrogen and alkyl; alternatively $R^A$ and $R^B$ are taken together with the N atom to which they are bound to form a heteroaryl or heterocycloalkyl group;

or a pharmaceutically acceptable salt thereof.

The present invention is further directed to a compound selected from the group consisting of 3-(4-benzyloxy-benzyl)-2-methyl-4-oxo-cyclohex-2-enecarboxylic acid ethyl ester 4-{4-hydroxymethyl-5-methyl-6-[4-(2-piperidin-1-yl-ethoxy)-benzyl]-cyclohex-1-enyl}-phenol and pharmaceutically acceptable salts thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating a disorder mediated by one or more estrogen receptors in a subject in need thereof comprising administering to the subject a therapeutically effective amount of any of the compounds or pharmaceutical compositions described above.

Illustrating the invention is a method of contraception comprising administering to a subject in need thereof co-therapy with a therapeutically effective amount of a compound of formula (I) with a progestogen or progestogen antagonist.

Another example of the invention is the use of any of the compounds described herein in the preparation of a medicament for treating: (a) hot flashes, (b) vaginal dryness, (c) osteopenia, (d) osteoporosis, (e) hyperlipidemia, (f) loss of cognitive function, (g) a degenerative brain disorder, (h) cardiovascular disease, (i) cerebrovascular disease j) breast cancer, (k) endometrial cancer, (l) cervical cancer, (m) prostate cancer, (n) benign prostatic hyperplasia, (o) endometriosis, (p) uterine fibroids, (q) osteoarthritis and for (r) contraception in a subject in need thereof.

DETAILED DESCRIPTION OF THE INVENTION

The present invention is directed to compounds of formula (I), (II) and (III)

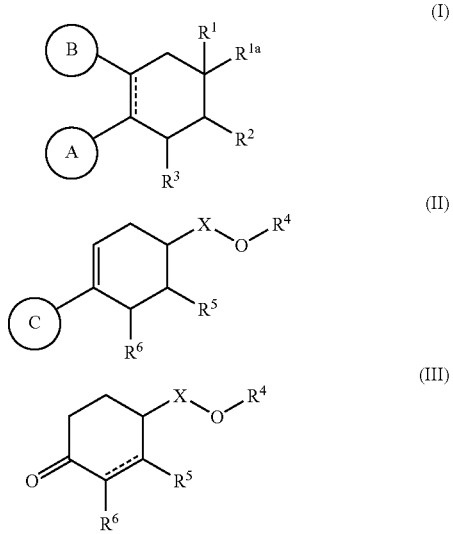

wherein

-----

$R^1$, $R^{1a}$, $R^2$, $R^3$, Ⓐ, Ⓑ, X, $R^4$, $R^5$, $R^6$ and Ⓒ are as herein defined. The compounds of the present invention are modulators of an estrogen receptor, useful for the treatment and prevention of disorders associated with estrogen depletion, including, but not limited to hot flashes, vaginal dryness, osteopenia, osteoporosis, hyperlipidemia, loss of cognitive function, degenerative brain diseases, cardiovascular and cerebrovascular diseases); for the treatment of hormone sensitive cancers and hyperplasia (in tissues including breast, endometrium, and cervix in women and prostate in men); for the treatment and prevention of endometriosis, uterine fibroids, and osteoarthritis; and as contraceptive agents either alone or in combination with a progestogen or progestogen antagonist.

In an embodiment of the present invention

----- is a single bond. In another embodiment of the present invention

===== is a double bond.

In an embodiment of the present invention $R^{1a}$ is selected from the group consisting of hydrogen and lower alkyl. Preferably $R^{1a}$ is selected from the group consisting of hydrogen and methyl.

In an embodiment of the present invention $R^1$ is selected from the group consisting of lower alkyl, hydroxy substituted lower alkyl, lower alkenyl, hydroxy substituted lower alkenyl, lower alkoxy-lower alkyl, lower alkoxy-carbonyl, lower alkyl-carbonyl, phenyl-carbonyl, lower alkyl-carbonyl-lower alkyl, $NR^AR^B$-carbonyl and $NR^AR^B$-lower alkoxy-lower alkyl. In another embodiment of the present invention $R^1$ is selected from the group consisting of lower alkyl, hydroxy substituted lower alkyl, hydroxy substituted lower alkenyl, lower alkoxy-lower alkyl, lower alkoxy-carbonyl, lower alkyl-carbonyl-lower alkyl and $NR^AR^B$-lower alkoxy-lower alkyl and $NR^AR^B$-carbonyl. Preferably, $R^1$ is selected from the group consisting of methyl, hydroxymethyl, 1-hydroxy-propyn-2-yl, 1-hydroxy-n-propyl, methoxymethyl, methoxycarbonyl, methylcarbonylmethyl, dimethylamino-ethoxy-methyl, morpholinyl-ethoxymethyl, morpholinylcarbonyl and diethylaminocarbonyl.

In an embodiment of the present invention, $R^A$ and $R^B$ are each independently selected from the group consisting of hydrogen and lower alkyl; alternatively $R^A$ and $R^B$ are taken together with the N atom to which they are bound to form a five to six membered heteroaryl or a five to six membered heterocycloalkyl group. Preferably, $R^A$ and $R^B$ are independently selected from the group consisting of hydrogen and methyl or are taken together with the nitrogen atom to which they are bound to form morpholinyl.

In an embodiment of the present invention, $R^2$ is selected from the group consisting of hydrogen, carboxy, lower alkyl, hydroxy substituted lower alkyl, lower alkenyl, hydroxy substituted lower alkenyl, lower alkoxy-lower alkyl, lower alkoxy-carbonyl, lower alkyl-carbonyl, phenyl-carbonyl, lower alkyl-carbonyl-lower alkyl, $NR^A R^B$-carbonyl and $NR^A R^B$-lower alkoxy-lower alkyl. In another embodiment of the present invention, $R^2$ is selected from the group consisting of hydrogen, carboxy, lower alkyl, hydroxy substituted lower alkyl, lower alkyl-carbonyl, lower alkoxy-lower alkyl, lower alkyl-carbonyl-lower alkyl and $NR^A R^B$-lower alkoxy-lower alkyl. Preferably, $R^2$ is selected from the group consisting of hydrogen, carboxy, methyl, hydroxymethyl, methoxycarbonyl, methoxymethyl, methylcarbonyl-methyl and dimethylamino-ethoxy-methyl.

In an embodiment of the present invention $R^1$ and $R^2$ are taken together with the atom to which they are bound to form a saturated ring structure of the formula;

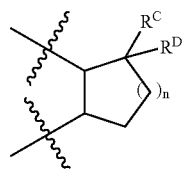

wherein n is an integer from 1 to 4.

In another embodiment of the present invention $R^1$ and $R^2$ are taken together with the atom to which they are bound to form a heteroatom containing saturated ring structure of the formula

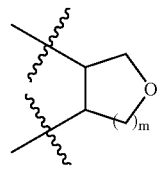

wherein m is an integer from 1 to 2.

Preferably, $R^1$ and $R^2$ are taken together with the atom to which they are bound to form a ring structure selected from the group consisting of 3-hydroxy-3-ethynyl-cyclopentyl, 3-hydroxy-cyclopentyl, 3-oxo-cyclopentyl, 3-hydroxy-cyclohexyl, 3-oxo-cyclohexyl, 3-oxo-cyclooctyl and dihydrofur-4-yl; wherein the $R^1+R^2$ ring is bound to the core structure through the 1,2-positions, numbering clockwise.

In an embodiment of the present invention $R^C$ and $R^D$ are independently selected from the group consisting of hydrogen, hydroxy, lower alkyl, lower alkynyl and lower alkoxy; alternatively $R^C$ and $R^D$ are taken together with the carbon atom to which they are bound to form an oxo group. In another embodiment of the present invention, $R^C$ and $R^D$ are independently selected from the group consisting of hydrogen, hydroxy and lower alkynyl; alternatively $R^C$ and $R^D$ are taken together with the carbon atom to which they are bound to form an oxo group.

In an embodiment of the present invention, $R^3$ is selected from the group consisting of hydrogen and lower alkyl. Preferably, $R^3$ is selected from the group consisting of hydrogen and ethyl.

In an embodiment of the present invention, Ⓐ is selected from the group consisting of aryl and heteroaryl; wherein the heteroaryl group is bound to the core structure through a carbon atom; and wherein the aryl or heteroaryl group is optionally substituted with one to two substitutents independently selected from hydroxy, lower alkoxy, aralkyl, aralkyloxy or $NR^A R^B$-lower alkoxy. In another embodiment of the present invention, Ⓐ is selected from the group consisting of aryl; wherein the aryl group is optionally substituted with a substituent selected from hydroxy, lower alkoxy and aralkyloxy. Preferably, Ⓐ is selected from the group consisting of phenyl, 4-hydroxyphenyl, 4-methoxyphenyl and 4-benzyloxy-phenyl.

In another embodiment of the present invention, Ⓐ is aryl; wherein the aryl group is optionally substituted with a substituent selected from hydroxy or lower alkoxy. Preferably, Ⓐ is selected from the group consisting of phenyl, 4-hydroxyphenyl and 4-methoxyphenyl.

In an embodiment of the present invention, Ⓑ is selected from the group consisting of aryl and heteroaryl; wherein the heteroaryl group is bound to the core structure through a carbon atom; and wherein the aryl or heteroaryl group is optionally substituted with one to two substitutents independently selected from hydroxy, lower alkoxy, aralkyl, aralkyloxy or $NR^A R^B$-lower alkoxy. In another embodiment of the present invention, Ⓑ is selected from the group consisting of aryl; wherein the aryl group is optionally substituted with one to two substituents independently selected from hydroxy, lower alkoxy, aralkyl and $NR^A R^B$-lower alkoxy. Preferably, Ⓑ is selected from the group consisting of phenyl, 4-hydroxyphenyl, 4-methoxyphenyl, 4-dimethylaminoethoxy-phenyl, 4-hydroxy-3-benzyl-phenyl and 4-(piperidinyl-ethoxy)-phenyl.

In another embodiment of the present invention, Ⓑ is aryl; wherein the aryl is optionally substituted with a substituent selected from lower alkoxy. Preferably, Ⓑ is selected from the group consisting of phenyl and 4-methoxyphenyl.

In an embodiment of the present invention, X is selected from the group consisting $C(O)$ and $CH_2$. Preferably, X is $C(O)$.

In an embodiment of the present invention, $R^4$ is selected from the group consisting of hydrogen and lower alkyl. In another embodiment of the present invention, $R^4$ is selected from the group consisting of lower alkyl. Preferably, $R^4$ is ethyl.

In an embodiment of the present invention, $R^5$ is selected from the group consisting of lower alkyl. Preferably, $R^5$ is methyl.

In an embodiment of the present invention, $R^6$ is selected from the group consisting of -(benzyl)-Q-(lower alkyl)-$NR^A R^B$. In another embodiment of the present invention, $R^6$ is selected from the group consisting of -(benzyl)-O-(lower alkyl)-$NR^A R^B$. Preferably, $R^6$ is selected from the group consisting of 4-(dimethylamino-ethoxy)-benzyl, 4-(morpholinyl-ethoxy)-benzyl, 4-(piperidinyl-ethoxy)-benzyl and 4-(pyrrolidinyl-ethoxy)-benzyl.

In an embodiment of the present invention, Q is selected from the group consisting of O and S. Preferably, Q is O.

In an embodiment of the present invention, $R^A$ and $R^B$ are each independently selected from the group consisting of hydrogen and lower alkyl; alternatively $R^A$ and $R^B$ are taken together with the N atom to which they are bound to form a five to six membered heteroaryl or a five to six membered heterocycloalkyl group. In another embodiment of the present invention, wherein $R^A$ and $R^B$ are each independently selected from lower alkyl; alternatively $R^A$ and $R^B$ are taken together with the N atom to which they are bound to form a five to six membered heteroaryl or five to six membered heterocycloalkyl group. Preferably, $R^A$ and $R^B$ are each methyl or are taken together with the N atom to which they are bound to form a morpholinyl, piperidinyl or pyrrolidinyl group.

In an embodiment of the present invention, Ⓒ is selected from the group consisting of aryl, aralkyl and heteroaryl; wherein the heteroaryl group is bound to the core structure through a carbon atom; and wherein the aryl, aralkyl or heteroaryl group is optionally substituted with one to two substitutents independently selected from halogen, hydroxy, alkoxy, aralkyloxy or $NR^AR^B$-alkoxy. In another embodiment of the present invention, Ⓒ is selected from the group consisting of aryl and heteroaryl; wherein the heteroaryl group is bound to the core structure through a carbon atom; and wherein the aryl or heteroaryl group is optionally substituted with a substituent selected from halogen, hydroxy or lower alkoxy. Preferably, Ⓒ is selected from the group consisting of 4-fluorophenyl, 4-hydroxyphenyl, 4-methoxyphenyl and 5-indolyl.

In an embodiment of the present invention is a compound selected from the group consisting of 3-(4-benzyloxy-benzyl)-2-methyl-4-oxo-cyclohex-2-enecarboxylic acid ethyl ester and 4-{4-hydroxymethyl-5-methyl-6-[4-(2-piperidin-1-yl-ethoxy)-benzyl]-cyclohex-1-enyl}-phenol.

In yet another embodiment of the present invention is a compound of formula (I) selected from group as listed in Table 1. In yet another embodiment of the present invention is a compound of formula (I) selected from group as listed in Table 2. In yet another embodiment of the present invention is a compound of formula (I) selected from group as listed in Table 3.

In an embodiment of the present invention is a compound of formula (II) selected from group as listed in Table 4. In another embodiment of the present invention is a compound of formula (III) selected from group as listed in Table 5.

Representative compounds of the present invention are as listed in Tables 1, 2, 3, 4 and 5. Unless otherwise noted, in the Tables below, in the column headed with the symbol " $\overline{\overline{\phantom{===}}}$ ", the notation 2 shall indicate a double bond, whereas the notation 1, shall indicate a single bond.

TABLE 1

| ID No | $R^{1a}$ | $R^1$ | $R^2$ | $R^3$ | Ⓐ | Ⓑ |
|---|---|---|---|---|---|---|
| 1 | methyl | hydroxymethyl | H | H | 4-hydroxyphenyl | 4-hydroxyphenyl |
| 2 | H | dimethylaminoethoxy-methyl | hydroxymethyl | H | 4-hydroxyphenyl | phenyl |
| 3 | methyl | hydroxymethyl | H | H | 4-hydroxyphenyl | 4-dimethylaminoethyloxyphenyl |
| 4 | H | hydroxymethyl | methyl | ethyl | 4-hydroxyphenyl | 4-methoxyphenyl |
| 5 | H | methoxymethyl | hydroxymethyl | H | 4-benzyloxyphenyl | phenyl |
| 6 | methyl | hydroxymethyl | H | H | 4-hydroxyphenyl | 4-dimethylaminoethyloxyphenyl |
| 7 | methyl | hydroxymethyl | H | H | 4-hydroxyphenyl | 4-hydroxyphenyl |

TABLE 2

| ID No | $R^{1a}$ | $R^1$ | $R^2$ | $R^3$ | Ⓐ | Ⓑ |
|---|---|---|---|---|---|---|
| 8 | H | methoxymethyl | methoxymethyl | H | 4-benzyloxyphenyl | phenyl |
| 9 | H | methylcarbonylmethyl | methylcarbonylmethyl | H | 4-benzyloxyphenyl | phenyl |
| 10 | H | morpholinylcarbonyl | carboxy | H | phenyl | phenyl |
| 11 | H | diethylaminocarbonyl | methoxycarbonyl | H | phenyl | phenyl |

TABLE 2-continued

| ID No | R$^{1a}$ | R$^1$ | R$^2$ | R$^3$ | Ⓐ | Ⓑ |
|---|---|---|---|---|---|---|
| 12 | methyl | 1-hydroxy-n-propyl | H | H | 4-methoxy-phenyl | 4-methoxy-phenyl |
| 13 | H | hydroxymethyl | hydroxymethyl | H | 4-benzyloxy-phenyl | H |
| 14 | H | morpholinyl-carbonyl | methoxy-carbonyl | H | phenyl | phenyl |
| 15 | H | dimethylamino-ethoxy-methyl | hydroxymethyl | H | 4-hydroxy phenyl | phenyl |
| 16 | H | hydroxymethyl | dimethylamino-ethoxy-methyl | H | 4-hydroxy-phenyl | phenyl |
| 17 | methyl | —CH(OH)—CCH | H | H | 4-methoxy-phenyl | 4-methoxy-phenyl |
| 18 (*) | H | hydroxymethyl | hydroxymethyl | H | phenyl | phenyl |
| 19 | H | morpholinyl ethoxymethyl | hydroxymethyl | H | 4-methoxy-phenyl | 4-methoxy-phenyl |
| 20 | H | hydroxymethyl | methyl | ethyl | 4-methoxy-phenyl | 4-hydroxy-phenyl |
| 21 | H | methoxymethyl | hydroxymethyl | H | 4-hydroxy-phenyl | phenyl |
| 22 | H | methoxy-carbonyl | methoxy-carbonyl | H | phenyl | phenyl |
| 23 | H | hydroxymethyl | H | H | phenyl | phenyl |
| 24 | H | methyl | methyl | H | 4-hydroxy-phenyl | phenyl |
| 25 | methyl | hydroxymethyl | H | H | 4-hydroxy-phenyl | H |
| 26 | H | hydroxymethyl | hydroxymethyl | H | 4-methoxy-phenyl | 4-methoxy-phenyl |
| 27 | methyl | hydroxymethyl | H | H | 4-hydroxy-phenyl | 4-hydroxy-phenyl |
| 28 | H | dimethylamino-ethoxy-methyl | hydroxymethyl | H | 4-benzyloxy-phenyl | phenyl |
| 29 | methyl | hydroxymethyl | H | H | 4-methoxy-phenyl | 4-methoxy-phenyl |
| 30 | methyl | hydroxymethyl | H | H | 4-methoxy-phenyl | 4-hydroxy-3-benzyl-phenyl |
| 31 | H | methyl | methyl | H | 4-benzyloxy-phenyl | phenyl |
| 32 | H | hydroxymethyl | hydroxymethyl | H | 4-hydroxy-phenyl | phenyl |
| 33 (#) | H | hydroxymethyl | hydroxymethyl | H | phenyl | phenyl |
| 34 | H | hydroxymethyl | methyl | H | phenyl | phenyl |
| 35 | H | diethylamino-carbonyl | carboxy | H | phenyl | phenyl |
| 36 | methyl | hydroxymethyl | methyl | H | phenyl | phenyl |
| 75 | H | hydroxymethyl | methyl | ethyl | 4-hydroxy-phenyl | 4-(piperidinyl-ethoxy)-phenyl |

(*) Indicates that the R$^1$ and R$^2$ groups are in a cis orientation relative to each other;
(#) Indicates that the R$^1$ and R$^2$ groups are in a trans orientation relative to each other.

TABLE 3

| ID No | ---- R¹ᵃ | R¹a | R¹ | A | B |
|---|---|---|---|---|---|
| 48 (##) | 2 | H | 3-hydroxy-3-ethynyl-cyclopentyl | 4-methoxy-phenyl | 4-methoxy-phenyl |
| 49 | 2 | H | 3-hydroxy-cyclopentyl | 4-methoxy-phenyl | H |
| 50 | 2 | methyl | 3-hydroxy-cyclopentyl | 4-methoxy-phenyl | H |
| 51 | 2 | H | 3-oxo-cyclopentyl | H | 4-hydroxy phenyl |
| 52 | 2 | H | dihydrofur-4-yl | phenyl | phenyl |
| 53 | 2 | H | 3-oxo-cyclooctyl | phenyl | phenyl |
| 54 | 2 | H | 3-oxo-cyclopentyl | 4-methoxy-phenyl | 4-methoxy-phenyl |
| 55 | 2 | H | 3-hydroxy-cyclopentyl | phenyl | H |
| 56 | 2 | H | 3-oxo-cyclohexyl | phenyl | phenyl |
| 57 (##) | 2 | H | 3-hydroxy-cyclopentyl | 4-methoxy-phenyl | 4-methoxy-phenyl |
| 58 (##) | 2 | H | 3-hydroxy-cyclohexyl | phenyl | phenyl |
| 59 (**) | 2 | H | 3-hydroxy-3-ethynyl-cyclopentyl | 4-methoxy-phenyl | 4-methoxy-phenyl |
| 60 (**) | 2 | H | 3-hydroxy-cyclohexyl | phenyl | phenyl |
| 61 (**) | 2 | H | 3-hydroxy-cyclopentyl | 4-methoxy-phenyl | 4-methoxy-phenyl |
| 62 | 2 | methyl | 3-oxo-cyclopentyl | 4-hydroxy-phenyl | H |
| 63 | 1 | H | 3-hydroxy-cyclohexyl | phenyl | phenyl |
| 64 | 2 | H | 3-oxo-cyclopentyl | 4-hydroxy-phenyl | H |
| 65 | 1 | H | 3-hydroxy-cyclopentyl | 4-hydroxy-phenyl | hydroxy |
| 66 | 2 | H | 3-hydroxy-cyclopentyl | 4-hydroxy-phenyl | H |
| 67 | 2 | H | 3-oxo-cyclopentyl | phenyl | phenyl |

(**) Indicates that in the substituent group wherein R¹ and R² are taken together with the carbon atoms to which they are bound to form a ring structure, the relative stereochemistry between the carbon atoms numbered 2 and 3 is cis.

(##) Indicates that in the substituent group wherein R¹ and R² are taken together with the carbon atoms to which they are bound to form a ring structure, the relative stereochemistry between the carbon atoms numbered 2 and 3 is trans.

TABLE 4

| ID No | R⁶ | C |
|---|---|---|
| 37 | 4-(dimethylamino-ethoxy)-benzyl | 5-indolyl |
| 38 | 4-(piperidinyl-ethoxy)-benzyl | 4-hydroxy phenyl |
| 39 | 4-(piperidinyl-ethoxy)-benzyl | 4-methoxy phenyl |
| 40 | 4-(dimethylamino-n-propoxy)-benzyl | 5-indolyl |
| 41 | 4-(morpholinyl-ethoxy)-benzyl | 5-indolyl |
| 42 | 4-(pyrrolidinyl-ethoxy)-benzyl | 4-hydroxy phenyl |
| 43 | 4-(piperidinyl-ethoxy)-benzyl | 5-indolyl |
| 44 | 4-(dimethylamino-ethoxy)-benzyl | 4-hydroxy phenyl |
| 45 | 4-(piperidinyl-ethoxy)-benzyl | 4-fluoro phenyl |
| 47 | 4-(pyrrolidinyl-ethoxy)-benzyl | 5-indolyl |

TABLE 5

| ID No | ---- | R⁶ |
|---|---|---|
| 68 | 1 | 4-(morpholinyl-ethoxy)-benzyl |
| 69 | 1 | 4-(dimethylamino-ethoxy)-benzyl |
| 70 | 1 | 4-(pyrrolidinyl-ethoxy)-benzyl |
| 71 | 2 | 4-(piperidinyl-ethoxy)-benzyl |
| 72 | 1 | 4-(dimethylamino-n-propoxy)-benzyl |

Additional compounds of the present invention, include:

73

74 wherein the compound #74, the hydroxymethyl, methyl and piperidinyl-ethoxy-benzyl substituents on the cyclohexene core are all in the cis conformation.

As used herein, "halogen" shall mean chlorine, bromine, fluorine and iodine.

As used herein, the term "alkyl" whether used alone or as part of a substituent group, include straight and branched chains, preferably, a chain containing one to eight carbon atoms. For example, alkyl radicals include, but are not limited to methyl, ethyl, propyl, isopropyl, butyl, isobutyl, sec-butyl, t-butyl, pentyl and the like. Unless otherwise noted, "lower" when used with alkyl means a carbon chain composition of 1–4 carbon atoms.

As used herein, unless otherwise noted, the term "alkenyl" whether used alone or as part of a substituent group, shall include straight and branched chains containing at least one unsaturated double bond. For example, vinyl, propenyl or allyl, butenyl, buten-2-yl, buten-3-yl, 2-methyl-buten-2-yl, and the like. Preferably, the alkenyl group containing two to eight carbon atoms. Unless otherwise noted, "lower" when used with alkenyl means a carbon chain composition of 2–4 carbon atoms.

As used herein, unless otherwise noted, the term "alkynyl" whether used alone or as part of a substituent group, shall include straight and branched chains containing at least one unsaturated triple bond. For example, ethynyl, propynyl, butyn-2-yl, and the like. Preferably, the alkynyl group containing two to eight carbon atoms. Unless otherwise noted, "lower" when used with alkynyl means a carbon chain composition of 2–4 carbon atoms.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Unless otherwise noted, "lower" when used with alkoxy means an alkoxy group comprising 1–4 carbon atoms.

As used herein, unless otherwise noted, "aryl" shall refer to unsubstituted carbocylic aromatic groups such as phenyl, naphthyl, and the like.

As used herein, unless otherwise noted, "aralkyl" shall mean any lower alkyl group substituted with an aryl group such as phenyl, naphthyl and the like. For example, benzyl, phenylethyl, phenylpropyl, naphthylmethyl, and the like.

As used herein, unless otherwise noted, the term "aralkyloxy" shall mean an aralkyl-O-group, wherein the aralkyl is as defined above and wherein the aralkyloxy group is bound through the O atom. Suitable examples include, but are not limited to benzyloxy, phenyl-ethoxy, and the like.

As used herein, unless otherwise noted, the term "cycloalkyl" shall mean any stable 3–8 membered monocyclic, saturated ring system, for example cyclopropyl, cyclobutyl, cyclopentyl, cyclohexyl, cycloheptyl and cyclooctyl.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, the term "heterocycloalkyl" shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heteroaryl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, dihydrofuryl, and the like. Preferred heterocycloalkyl groups include dihydrofuryl, morpholinyl, piperidinyl, and pyrrolidinyl.

When a particular group is "substituted" (e.g., Ph, aryl, heteroaryl, heteroaryl), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

Unless otherwise noted, when naming the substituent group wherein $R^1$ and $R^2$ are taken together with the carbon atoms to which they are bound to form a ring structure, said substituent group—the rightmost ring structure of the bicyclic structure of compounds of formula (Iaa) or (Iab)

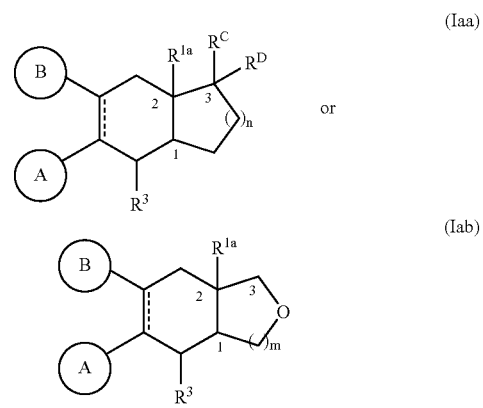

shall be named such that the bridging carbon atoms are numbered 1 and 2 and any $R^C$ and/or $R^D$ substituents are bound at the carbon atom numbered 3. Remaining carbon and/or oxygen atoms within the substituent group wherein $R^1$ and $R^2$ are taken together with the carbon atoms to which they are bound to form a ring structure, will be numbered in order, counting clockwise.

Under standard nomenclature used throughout this disclosure, the terminal portion of the designated side chain is described first, followed by the adjacent functionality toward the point of attachment. Thus, for example, a "phenyl$C_1$–$C_6$alkylaminocarbonyl$C_1$–$C_6$alkyl" substituent refers to a group of the formula

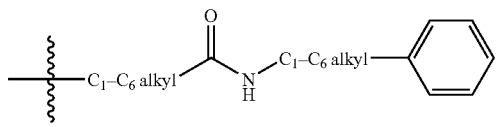

Abbreviations used in the specification, particularly the Schemes and Examples, are as follows:

| | |
|---|---|
| $Bu_3SnH$ = | Tributyl Tin Hydride |
| DCM = | Dichloromethane |
| DIBAL-H = | Diisobutyl aluminum hydride |
| DIPEA = | Di-isopropylethylamine |
| DMEM = | Dulbecco's Modified Eagle Medium (Gibco) |
| DMF = | N,N-Dimethylformamide |
| DMSO = | Dimethylsulfoxide |
| DTT = | Dithiothreitol |
| $Et_2O$ = | Diethyl Ether |
| EtOH = | Ethanol |
| HEPES = | 4-(2-Hydroxyethyl)-1-Piperizine Ethane Sulfonic Acid |
| HPLC = | High Pressure Liquid Chromatography |
| KHMDS = | Potassium Bis(trimethylsilyl) amide |
| KOtBu = | Potassium t-butoxide |
| LAH = | Lithium aluminum hydride |
| LDA = | Lithium diisopropylamide |
| LHMDS = | Lithium Bis(trimethylsilyl) amide |
| MeOH = | Methanol |
| nBuLi = | n-Butyl lithium |
| NMR = | Nuclear Magnetic Resonance |
| PBS = | Phosphate Buffered Saline |
| $Pd(dppf)Cl_2$ = | dichloro[1,1'-bis(diphenyl-phosphino)-ferrocene] palladium (II) |
| $Pd_2Cl_2(PPh_3)_2$ = | Palladium Bis(triphenylphosphine) chloride |
| $Pd(PPh_3)_4$ = | tetrakistriphenylphosphine palladium (0) |
| TBS = | t-Butyldimethylsilane |
| TBSCl = | t-Butyldimethylchlorosilane |
| tBuOH = | t-butanol |
| TEA = | Triethylamine |
| THF = | Tetrahydrofuran |
| TIPS = | Triisopropylsilane CORRECT??? |
| TLC = | Thin Layer Chromatography |
| TMSCl = | Trimethylsilyl chloride |
| TsCl = | Tosyl chloride |

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. Wherein the present invention directed to co-therapy comprising administration of one or more compound(s) of formula (I), compound(s) of formula (II) and/or compound(s) of formula (III) and a progestogen or progestogen antagonist, "therapeutically effective amount" shall mean that amount of the combination of agents taken together so that the combined effect elicits the desired biological or medicinal response. For example, the therapeutically effective amount of co-therapy comprising administration of a compound of formula (I) and progestogen would be the amount of the compound of formula (I) and the amount of the progestogen that when taken together or sequentially have a combined effect that is therapeutically effective. Further, it will be recognized by one skilled in the art that in the case of co-therapy with a therapeutically effective amount, as in the example above, the amount of the compound of formula (I) and/or the amount of the progestogen or progestogen antagonist individually may or may not be therapeutically effective.

As used herein, the term "co-therapy" shall mean treatment of a subject in need thereof by administering one or more compounds of formula (I), compounds of formula (II) and/or compounds of formula (III) with a progestogen or progestogen antagonist, wherein the compound(s) of formula (I), compound(s) of formula (II), or compound(s) of formula (III) and the progestogen or progestogen antagonist are administered by any suitable means, simultaneously, sequentially, separately or in a single pharmaceutical formulation. Where the compound(s) of formula (I), compound(s) of formula (II), compound(s) of formula (III) and the progestogen or progestogen antagonist are administered in separate dosage forms, the number of dosages administered per day for each compound may be the same or different. The compound(s) of formula (I), compound(s) of formula (II), compound(s) of formula (III) and the progestogen or progestogen antagonist may be administered via the same or different routes of administration. Examples of suitable methods of administration include, but are not limited to, oral, intravenous (iv), intramuscular (im), subcutaneous (sc), transdermal, and rectal. Compounds may also be administered directly to the nervous system including, but not limited to, intracerebral, intraventricular, intracerebroventricular, intrathecal, intracisternal, intraspinal and/or perispinal routes of administration by delivery via intracranial or intravertebral needles and/or catheters with or without pump devices. The compound(s) of formula I, compound(s) of formula (II), compound(s) of formula (III) and the progestogen or progestogen antagonist may be administered according to simultaneous or alternating regimens, at the same or different times during the course of the therapy, concurrently in divided or single forms.

As used herein, the term "composition" is intended to encompass a product comprising the specified ingredients in the specified amounts, as well as any product which results, directly or indirectly, from combinations of the specified ingredients in the specified amounts.

As used herein, the term "disease or disorder modulated by an estrogen receptor" shall mean any disease or disorder which is mediated by the estrogen α, any disease or disorder which is mediated by the estrogen β receptor or any disease or disorder which is mediated by both the estrogen α and estrogen β receptors. For example, hot flashes, vaginal dryness, osteopenia, osteoporosis, hyperlipidemia, loss of cognitive function, a degenerative brain disorder, cardiovascular disease, cerebrovascular disease breast cancer, endometrial cancer, cervical cancer, prostate cancer, benign prostatic hyperplasia (BPH), endometriosis, uterine fibroids, osteoarthritis and contraception.

As used herein, the term "degenerative brain disease" shall include cognitive disorder, dementia, regardless of underlying cause and Alzheimer's disease.

As used herein, the term "cardiovascular disease" shall include elevated blood lipid levels, coronary arthrosclerosis and coronary heart disease.

As used herein, the term "cerebrovascular disease" shall include abnormal regional cerebral blood flow and ischemic brain damage.

Compounds of formula (I) wherein $R^1$ and $R^2$ are not taken together with the atoms to which they are bound to form a ring structure and wherein R1 is selected from the group consisting of hydroxy-methyl and $NR^AR^B$-alkoxy-methyl may be prepared according to the process outlined in Scheme 1.

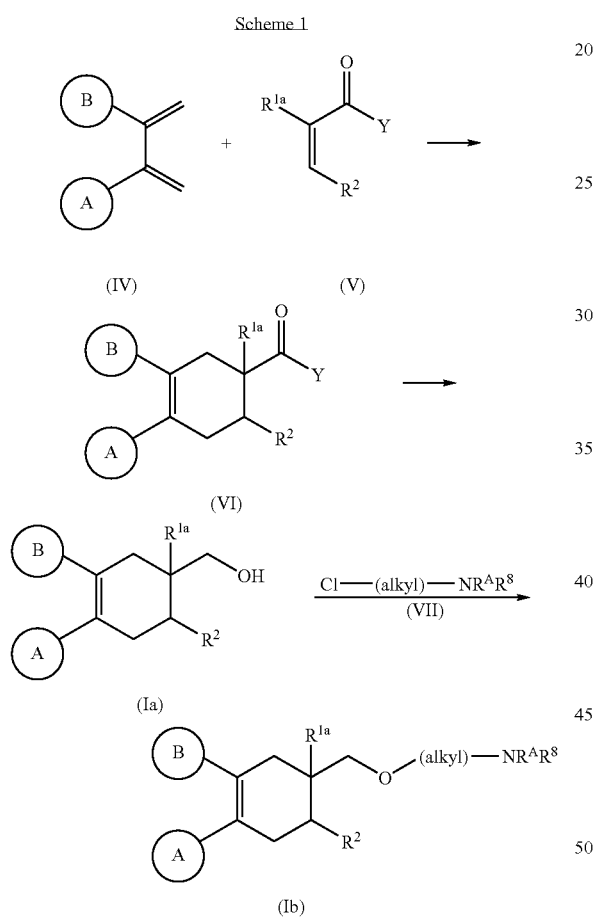

Accordingly, a suitably substituted compound of formula (IV), a known compound or compound prepared by known methods is reacted with a suitably substituted compound of formula (V), wherein Y is hydrogen, lower alkyl (such as methyl, ethyl) or lower alkoxy (such as methoxy, ethoxy), a known compound or compound prepared by known methods, in the presence of a Lewis acid such as $BF_3$.Etherate, tin tetrachloride, titanium tetrachloride, magnesium bromide, and the like, preferably at a temperature in the range of about −78 to about 0° C., in an organic solvent such as methylene chloride, chloroform, acetonitrile, toluene, and the like, to yield the corresponding compound of formula (VI).

The compound of formula (VI) is reduced by reacting with a suitable reducing agents such as LAH, $BH_3$, lithium borohydride, sodium borohydride, DiBAL-H, and the like, to yield the corresponding compound of formula (Ia).

The compound of formula (Ia) is optionally further reacted with a suitably substituted compound of formula (VII), a known compound or compound prepared by known methods, in the presence of a strong base such as NaH, LiHMDS, NaHMDS, n-butyl lithium, and the like, in an organic solvent such as THF, dioxane, and the like, to yield the corresponding compound of formula (Ib).

Compounds of formula (I) wherein $R^1$ is selected from the group consisting of alkyl, hydroxy substituted alkyl, alkenyl, hydroxy substituted alkenyl, alkynyl, hydroxy substituted alkynyl, alkoxyalkyl, alkoxy-carbonyl, alkyl-carbonyl, aryl-carbonyl, heteroaryl-carbonyl, heterocycloalkyl-carbonyl, alkyl-carbonyl-alkyl, $NR^ARB$-carbonyl, $NR^AR^B$-alkoxy-alkyl may be prepared by reacting a suitably substituted compound of formula (VI) wherein Y is H or a lower alkyl by reacting the compound of formula (VI) wherein Y is H or lower alkyl with a suitably substituted nucleophile, a known compound or compound prepared by known methods, in an organic solvent such as THF, dioxane, and the like.

One skilled in the art will recognize that compounds of formula (I) wherein $R^3$ is alkyl may be similarly according to the process described in Scheme 1 above, by substituting a suitably substituted compound of formula (IVa)

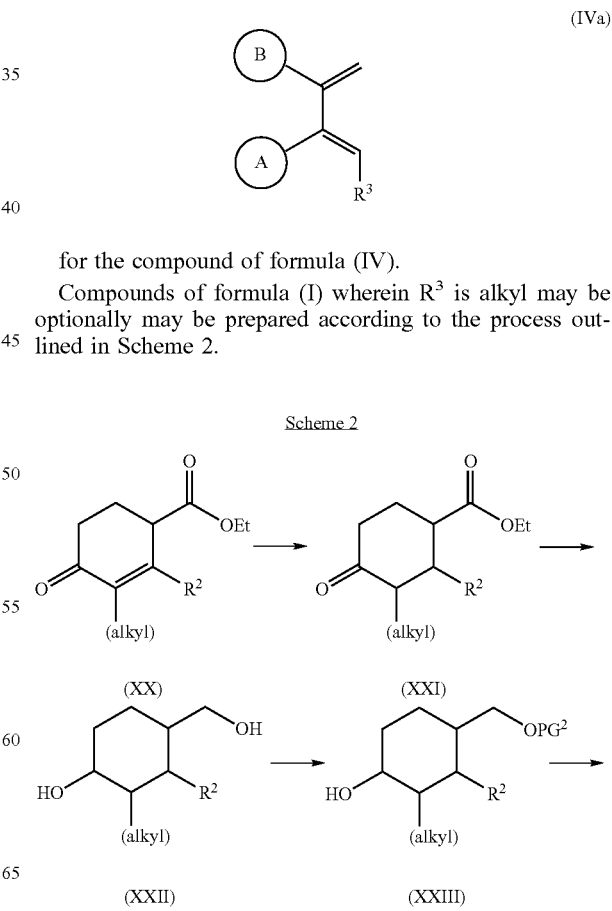

for the compound of formula (IV).

Compounds of formula (I) wherein $R^3$ is alkyl may be optionally may be prepared according to the process outlined in Scheme 2.

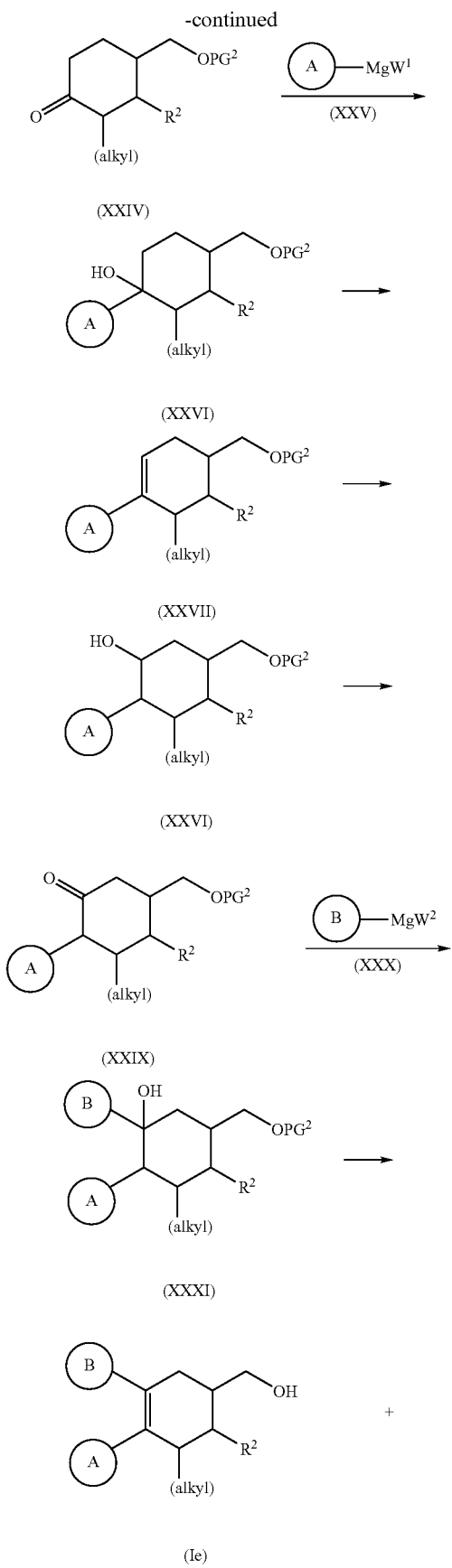
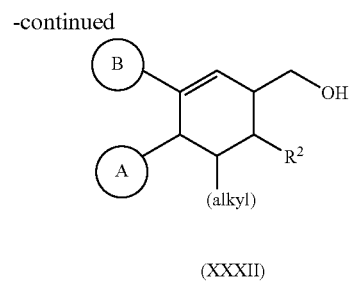

Accordingly, a suitably substituted compound of formula (XX), a known compound or compound prepared by known methods, is reduced with a suitable reducing agent such as hydrogen gas, in the presence of a catalyst such as Pd on carbon, in an organic solvent such as ethyl acetate, methanol, ethanol, isopropyl alcohol, and the like, to yield the corresponding compound of formula (XXI).

The compound of formula (XXI) is reacted with a reducing agent such as LAH, DiBAL-H, borane or source of borane, and the like, in an organic solvent such as THF, dioxane, and the like, to yield the corresponding compound of formula (XXII).

One skilled in the art will recognize that the reduction of the double bond, carbonyl and ester groups on the compound of formula (XX) may alternatively be completed in any order and/or in one or more steps, according to known methods other than those described herein, to yield the corresponding compound of formula (XXII).

The compound of formula (XXII) is reacted with a suitable protecting group reagent, according to known methods, to yield the corresponding compound of formula (XXIII), wherein $PG^2$ is the corresponding protecting group such as TBS, TIPS, and the like. For example, the compound of formula (XXII) may be reacted with TBSCI in the presence of a base such as TEA, DIPEA, pyridine, and the like, to yield the corresponding compound of formula (XXIII), wherein $PG^2$ is TBS.

The compound of formula (XXIII) is oxidized according to known methods, to yield the corresponding compound of formula (XXIV). For example, the compound of formula (XXIII) may be subjected to Swern oxidation by reacting with $(COCl)_2$ in DMSO in the presence of TEA, to yield the corresponding compound of formula (XXIV).

The compound of formula (XXIV) Is reacted suitably substituted compound of formula (XXV), a known compound or compound prepared by known methods, wherein $W^1$ is Br or Cl, in an anhydrous organic solvent such as THF, dioxane, and the like, to yield the corresponding compound of formula (XXVI).

The compound of formula (XXVI) is subjected to dehydration by reacting with an acid such as trifluoroacetic acid, p-toluenesulfonic acid, and the like, to yield the corresponding compound of formula (XXVII).

The compound of formula (XXVII) is reacted in a two step process, first with borane or a source of borane such as $BH_3.S(CH3)_2$, Catecol borane, 9-BBN, and the like, in an organic solvent such as THF, dioxane, diethyl ether, and the like; and then reacted with peroxide in the presence of a base such as NaOH, LiOH, KOH, and the like, in an organic solvent such as THF/water mixture, ethanol, methanol, and the like, to yield the corresponding compound of formula (XXVIII).

The compound of formula (XXVIII) is oxidized according to known methods, to yield the corresponding compound of formula (XXIX). For example, the compound of formula (XXVIII) may be subjected to Swern oxidation by reacting with $(COCl)_2$ in DMSO in the presence of TEA, to yield the corresponding compound of formula (XXIX).

The compound of formula (XXIX) is reacted with a suitably substituted compound of formula (XXX), a known compound or compound prepared by known methods, wherein $W^2$ is Br or Cl, in an anhydrous organic solvent such as THF, dioxane, and the like, to yield the corresponding compound of formula (XXXI).

The compound of formula (XXXI) is is subjected to dehydration by reacting with an acid such as trifluoroacetic acid, p-toluenesulfonic acid, and the like, to yield a mixture of the compound of formula (XXXII) and the compound of formula (Ie).

Preferably, the mixture of the compound of formula (XXXII) and the compound of formula (Ie) is separated, according to known methods, to isolate the compound of formula (Ie).

Compounds of formula (I) wherein $R^1$ and $R^2$ are taken together with the atoms to which they are bound to form a five to eight membered saturated ring structure, wherein the saturated ring structure does not contain a heteroatom selected from O, N or S, may be prepared according to the process outlined in Scheme 3.

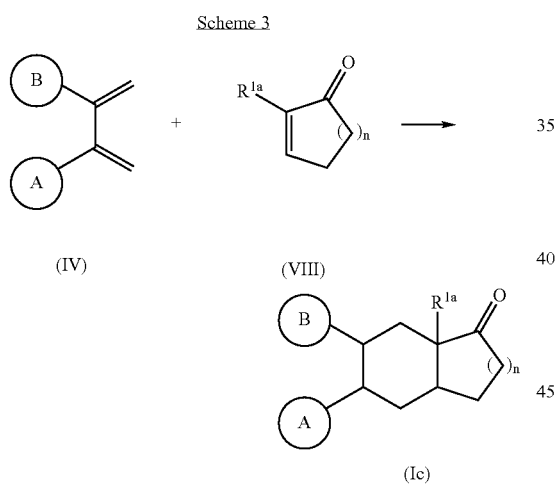

Accordingly, a suitably substituted compound of formula (IV), a known compound or compound prepared by known methods, is reacted with a suitably substituted compound of formula (VIII), wherein the n is an integer from 1 to 4 a known compound or compound prepared by known methods, in the presence of a Lewis acid such as BF.Etherate, tin tetrachloride, titanium tetrachloride, magnesium bromide, and the like, preferably at a temperature in the range of about −78 to about 0° C., in an organic solvent such as methylene chloride, chloroform, acetonitrile, toluene, and the like, to yield the corresponding compound of formula (Ic).

One skilled in the art will recognize that the carbonyl on the compound of formula (Ic) may be optionally, further reacted with a suitably substituted nucleophile. For example, the compound of formula (Ic) may be reacted with with a vinyl magnesium chloride or with vinyl magnesium bromide, to yield the corresponding compound of formula (Id)

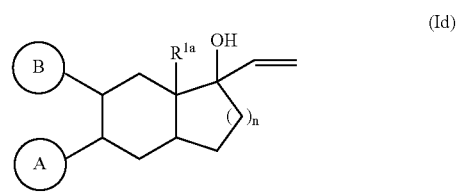

Compounds of formula (I) wherein $R^1$ and $R^2$ are taken together with the atoms to which they are bound to a group of the formula

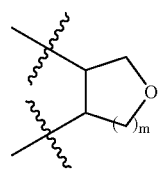

may be prepared according to the process outlined in Scheme 4.

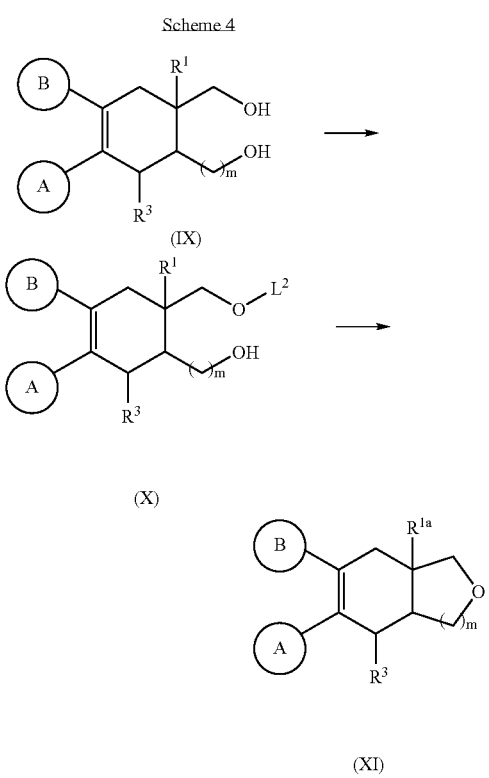

Accordingly, a suitably substituted compound of formula (IX), a known compound or compound prepared by known methods, is reacted according to known methods (or example the compound of formula (IX) is reacted with mesityl chloride or tosyl chloride, in the presence of a base such as TEA, DIPEA<pyridine, and the like), to yield the corresponding compound of formula (X), wherein $L^2$ is a suitable leaving group such as mesyl, tosyl, and the like.

The compound of formula (X) is subjected to ring closure by reacting with a base such as $K_2CO_3$, NaOH, $NaOCH_3$, and the like, to yield the corresponding compound of formula (XI).

One skilled in the art will recognize that compounds of formula (I) wherein ----- is a single bond may be prepared by reducing the corresponding compound of formula (I) wherein ----- is a double bond, by known methods, for example by reacting with hydrogen gas, in the presence of a catalyst such as 10% palladium on carbon, platinum, and the like, wherein the hydrogen gas is added at a pressure in the range of about 5 to about 50 psi, preferably about 30 psi, in an organic solvent such as ethanol, ethyl acetate, and the like.

Compounds of formula (III) wherein $R^4$ is hydrogen and

----- is a double bond may be prepared according to the process outlined in Scheme 5.

Scheme 5

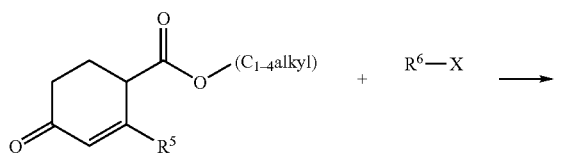

(L)        (LI)

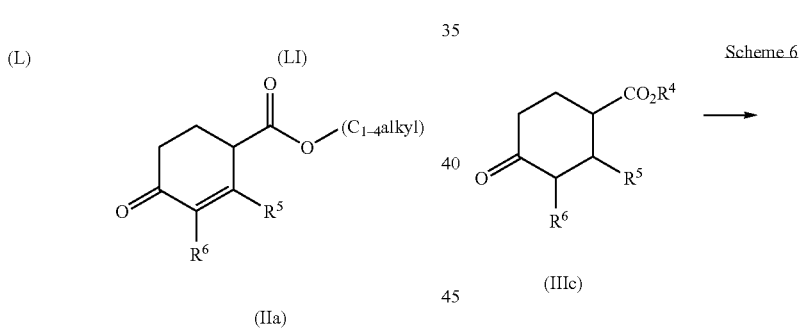

(IIa)

Accordingly, a suitably substituted compound of formula (L) (wherein the $C_{1-4}$alkyl is preferably ethyl) is reacted with a suitably substituted compound of formula (LI), a known compound or compound prepared by known methods is reacted with a suitably substituted compound of formula (V), wherein X is chloro, iodo or bromo, a known compound or compound prepared by known methods, in the presence of a base such as potassium-t-butoxide, sodium ethoxide, sodium t-butoxide and the like, in an organic solvent such as t-butanol, ethanol, and the like, to yield the corresponding compound of formula (IIIa).

One skilled in the art will recognize that the compound of formula (IIIa) may further optionally be reduced by known methods, for example with hydrogen gas, in the presence of a catalyst such as 10% palladium on carbon, platinum, and the like, wherein the hydrogen gas is added at a pressure in the range of about 5 to about 50 psi, preferably about 30 psi, in an organic solvent such as ethanol, ethyl acetate, and the like, to yield the corresponding compound of formula (IIIb)

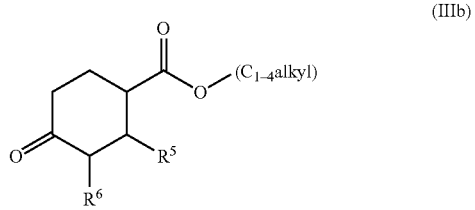

a compound of formula (III) wherein

----- is a single bond.

One skilled in the art will further recognize that the compound of formula (IIIa) or the compound of formula (IIIb) may be optionally further reacted, according to known methods (for example with a strong base such as NaOH, LiOH, and the like, in a solvent mixture such as THF/water, ethanol/water, and the like) to convert the ester portion (i.e the —C(O)—O—($C_{1-4}$alkyl) portion) to the corresponding carboxy group (i.e. —C(O)OH group).

Compounds of formula (II) may be prepared according to the process outlined in Scheme 6.

Scheme 6

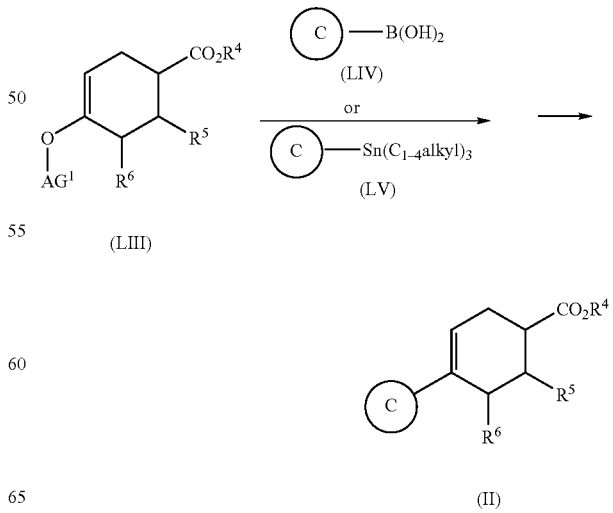

Accordingly, a suitably substituted compound of formula (IIIc), wherein $R^4$ is selected from the group consisting of hydrogen and lower alkyl, a compound prepared according to any of the processes described above, is reacted with a suitable activating reagent, such as triflic anhydride, N-phenyltrifluoromethane sulfonamide, N,N-bis(trifluoromethylsulfonyl)amino-5-chloro-pyridine, and the like, in the presence of a base such as LHMDS, KHMDS, LDA, and the like, in an aprotic solvent such as THF, diethyl ether, 1,4-dioxane, and the like, to yield the corresponding compound of formula (LIII), wherein AG1 is the corresponding activating group to the activating reagent. (For example, when the activating reagent is triflic anhydride, $OAG^1$ is triflate).

The compound of formula (LIII) is reacted with a suitably substituted boronic acid, a compound of formula (LIV), a known compound or compound prepared by known methods, or with a suitably substituted trialkyl tin, a compound of formula (LV), a known compound or compound prepared by known methods, in the presence of a catalyst such as $Pd(PPh_3)_4$, $Pd(PPh_3)_2Cl_2$, $Pd(dppf)Cl_2$, and the like, in the presence of a base such as $K_3PO_4$, TEA, DIPEA, and the like, in an organic solvent such as 1,4-dioxane, THF, DMF, toluene, and the like, to yield the corresponding compound of formula (II).

The following Examples are set forth to aid in the understanding of the invention, and are not intended and should not be construed to limit in any way the invention set forth in the claims which follow thereafter.

EXAMPLE 1

4-(4-Hydroxy-phenyl)-[4-(2-morpholin-4-yl-ethoxy)-benzyl]-methyl-cyclohex-3-enecarboxylic acid ethyl ester Compound #38

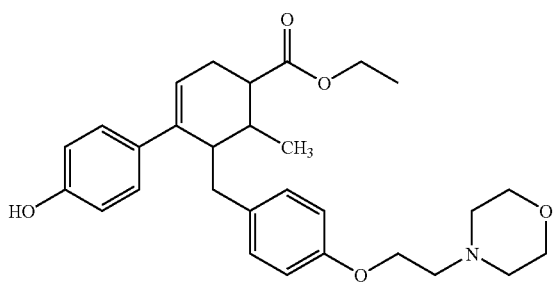

A solution of vinyl triflate (70 mg, 0.1309 mmol) and $K_3PO_4$ (42 mg, 0.1946 mmol) in 1,4-dioxane (2 mL) was degassed by bubbling Ar(g) through the solution for 15 minutes. To the degassed solution was then added 4-hydroxyphenyl boronic acid (20 mg, 0.1440 mmol) and $Pd(PPh_3)_4$ (4 mg, $3.27 \times 10^{-3}$ mmol) and the reaction mixture was heated at 80° C. for 16 hours. The reaction mixture was then concentrated and purified by preparatory TLC using 5% $MeOH/CH_2Cl_2$ to elute, to yield the title compound as a foam.

MS (M+1) 478.1.

EXAMPLE 2

4-(4-Hydroxymethyl-4-methyl-cyclohex-1-enyl)-phenol Compound #25

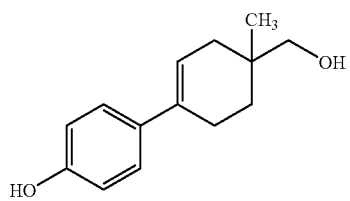

4-benzyloxy iodobenzene (193 g, 0.625 mol), ethynyl-trimethyl-silane (75 g, 0.76 mol), CuI (2 g, 10.5 mmol) and $Pd(PPh_3)_2Cl_2$ (1 g, 1.0 mmol) were added to diethylamine (880 mL) at 0° C. The reaction mixture was warmed to 25° C. and then stirred for 6 h. The reaction mixture was concentrated and partitioned in $H_2O$/ethyl acetate (100 mL/100 mL). The reaction mixture was further extracted with ethyl acetate (300 mL×2). The combined organic layers were washed by water (300 mL), dried over $MgSO_4$ and concentrated in vacuo. The crude product was dissolved in methanol (400 mL) and was stirred with KOH (28 g, 0.5 mol) for 1 h at 25° C. Concentration and purification by silica gel column chromatograph (5% ethyl acetate/Hexane) yielded 4-benzyloxy phenyl acetylene as liquid.

To a suspended solution of NaI (70 g, 0.46 mol) and 4-benzyloxy phenyl acetylene (40 g, 0.0956 mol) was added $H_2O$ (26 mL). The reaction mixture was then cooled to 0° C. TMSCl (60 mL, 0.475 mol) was added slowly to maintain the temperature at 0° C. The reaction mixture was then stirred for another 3 h at 0° C. The reaction mixture was quenched by adding saturated aqueous $NaHCO_3$ (200 mL), followed by dilution with ethyl acetate (600 mL). The combined organic layers were washed by $NaHCO_3$ solution, dried over $Na_2SO_4$, and purification on $SiO_2$ (2%~5% ethyl acetate/hexane) to yield 1-benzyloxy-4-(1-iodo-vinyl)-benzene.

1-benzyloxy-4-(1-iodo-vinyl)-benzene (12.0 g, 0.035 mol), vinyl tributyl tin (16.0 mL, 0.056 mol) and $PdCl_2(CH_3CN)_2$ (150 mg, 0.0579 mmol) were dissolved in DMF (300 mL). The reaction mixture was stirred at 25° C. for 16 h, then partitioned between ethyl acetate (800 mL) and $H_2O$ (400 mL). The organic layer was washed by brine, concentrated and purified on $SiO_2$ (15% ethyl acetate/Hexane) to yield 1-benzyloxy-4-(1-methylene-allyl)-benzene.

MS (m/z): 237 ($MH^+$), 235 ($MH^-$).

1-benzyloxy-4-(1-methylene-allyl)-benzene (0.40 g, 1.694 mmol) and 2-methyl-propenal (0.355 mL) in DCM (10 mL) was cooled to −10° C. $BF_3.OCH_2CH_3$ (0.322 mL, 1.778 mmol) was added and the reaction mixture stirred for 3 h. The mixture was then quenched by aqueous saturated $NaHCO_3$ solution. After extraction with ethyl acetate (2×100 mL), the reaction mixture was dried over $MgSO_4$ and purified on $SiO_2$ to yield 4-(4-benzyloxy-phenyl)-1-methyl-cyclohex-3-ene carbaldehyde.

MS (m/z): 307 ($MH^+$), 305 ($MH^-$).

To a cooled solution of 4-(4-benzyloxy-phenyl)-1-methyl-cyclohex-3-ene carbaldehyde (0.41 g, 1.33 mmol) in THF (10.0 mL) was added to LAH (0.100 g, 2.70 mmol) and the reaction mixture stirred at 0° C. for 3 h. The reaction mixture was then quenched by methanol followed by aqueous HCl (1N, 2 mL) until all of the black/brown precipitate was dissolved. The resulting mixture was extracted with ethyl acetate (2×30 mL). The combined organic layers were washed with brine, dried over MgSO$_4$ and purified by SiO$_2$ (50% ethyl acetate/hexane) to yield [4-(4-benzyloxy-phenyl)-1-methyl-cyclohex-3-enyl]-methanol as a liquid.

MS (m/z): 309 (MH$^+$), 307 (MH$^-$)

To a solution of [4-(4-benzyloxy-phenyl)-1-methyl-cyclohex-3-enyl]-methanol (102 mg, 0.331 mmol) in DCM (5.0 mL) at −78° C. was added BCl$_3$ (1.0 M in hexanes, 0.5 mL). The reaction mixture was then stirred at −78° C. for 3 h. The mixture was then quenched with aqueous saturated NaHCO$_3$ (30 mL), extracted with ethyl acetate (60 mL), dried over MgSO$_4$ and purified by SiO$_2$ (50~70% ethyl acetate/Hexanes) to yield 4-(4-hydroxymethyl-4-methyl-cyclohex-1-enyl)-phenol as a liquid.

MS (m/z): 219 (MH$^+$), 217 (MH$^-$).

EXAMPLE 3 and 4-{2-[4-(2-Dimethylamino-ethoxy)-phenyl]-4-hydroxymethyl-4-methyl-cyclohex-1-enyl}-phenol Compound #27 and #3

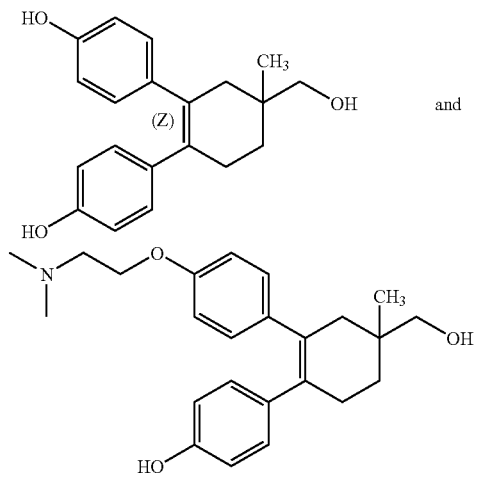

1-benzyloxy-4-ethynyl-benzene (70 g, 0.3365 mol), Bu$_3$SnH (59 mL, 0.3365 mol) and Ph(PP$_3$)$_2$Cl$_2$ (120 mg, 0.1718 mmol) were stirred in THF (500 mL) at 25° C. for 16 h and then refluxed for 1 h. The resulting solution was concentrated and then purified on SiO$_2$ (2% ~5% ethyl acetate/hexane) to yield tributyl-[1-(4-benzyloxy-phenyl)-vinyl]-stannane.

To a cooled solution of tributyl-[1-(4-benzyloxy-phenyl)-vinyl]-stannane (26.2 g, 52.6 mmol) in DMF (180 mL) at 0° C. was added CuCl (8.6 g, 87.7 mmol) and CuCl$_2$ (1.00 g, 8.13 mmol), which was then stirred at 25° C. for 2 h. The reaction mixture was then diluted with ethyl acetate (500 mL) and washed with brine (3×300 mL). The reaction mixture was then dried over MgSO$_4$ and purified by SiO$_2$ (20% ethyl acetate/hexane) to yield 2,3-di(4-benzyloxy-phenyl)-1,3-butadiene.

MS (m/z): 419 (MH$^+$), 417 (MH$^-$).

To a solution of 2,3-di(4-benzyloxy-phenyl)-1,3-butadiene (1.2 g, 2.8 mmol) and 2-methyl-propenal (0.602 g, 8.4 mmol) in DCM (10.5 mL) was added BF$_3$.OCH$_2$CH$_3$ (0.596 mL, 4.2 mmol) at −10° C. After 3 h at −10° C., the reaction mixture was quenched with saturated aqueous NaHCO$_3$ (10 mL). The reaction mixture was then extracted with ethyl acetate (2 10 mL), dried over MgSO$_4$ and purified by SiO$_2$ twice (15% ethyl acetate/hexane) to yield 1-methyl-3,4-di(4-benzyloxy-phenyl )-cyclohex-3-ene carbaldehyde.

MS (m/z): 489 (MH$^+$), 487 (MH$^-$).

To a solution of 1-methyl-3,4-di(4-benzyloxy-phenyl)-cyclohex-3-ene carbaldehyde (200 mg, 0.409 mmol) in MeOH (10.0 mL) at −10° C. was added NaBH$_4$ (100 mg, excess). The reaction mixture was stirred 30 min and then quenched with 51% HCl solution (5 mL), extracted with ethyl acetate (50 mL) and dried over MgSO$_4$. The reaction mixture was then concentrated and purified on SiO$_2$ (50% ethyl acetate/hexane) to yield (1-methyl-3,4-di(4-benzyloxy-phenyl)-cyclohex-3-enyl)-methanol.

MS (m/z): 491 (MH$^+$), 489 (MH$^-$)

To a solution of (1-methyl-3,4-di(4-benzyloxy-phenyl)-cyclohex-3-enyl)-methanol (150 mg, 0.306 mmol) in DCM (5.0 mL) at −10° C. was added TiCl$_4$ (0.102 mL, 3.0 eq.) and the reaction mixture stirred at −10° C. for 3 h. The reaction mixture was then diluted with ethyl acetate (20 mL and H$_2$O (10 mL). The organic layer was separated, dried over MgSO$_4$, and purified by SiO$_2$ (50~100% ethyl acetate/hexane) to yield a lower TLC spot of (1-methyl-3,4-di(4-hydroxy-phenyl)-cyclohex-3-enyl)-methanol.

MS (m/z): 311 (MH$^+$), 309 (MH$^-$).

To a solution of (1-methyl-3,4-di(4-hydroxy-phenyl)-cyclohex-3-enyl)-methanol (30 mg, 1 eq.) in DMF (1 mL) was added NaH (10 mg, 1 eq.), and the reaction mixture was then stirred for 2 h at 25° C. To the reaction mixture was then added (2-chloro-ethyl)-dimethyl-amine (12 mg, 1 eq) and the mixture stirred for 16 hours. The reaction mixture was then partitioned between H$_2$O/ethyl acetate (5 mL/5 mL). The organic layer was separated, dried over MgSO$_4$, concentrated and purified HPLC (20%~80% CH$_3$CN/H$_2$O with 0.1% TFA) to yield 4-{2-[4-(2-dimethylamino-ethoxy)-phenyl]-4-hydroxymethyl-4-methyl-cyclohex-1-enyl}-phenol.

MS (m/z): 382 (MH$^+$), 380 (MH$^-$).

EXAMPLE 4

4-[6-Ethyl-4-hydroxymethyl-2-(4-methoxy-phenyl)-5-methyl-cyclohex-1-enyl]-phenol and 4-[2-Ethyl-4-hydroxymethyl-6-(4-methoxy-phenyl)-3-methyl-cyclohexyl]-phenol Compound #20 and #4

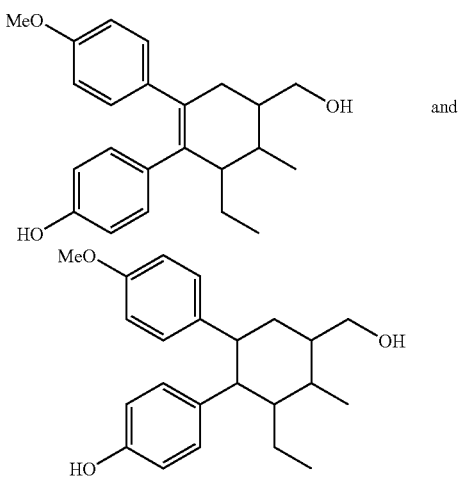

To 2-ethyl-4-hydroxymethyl-3-methyl-cyclohexanol (30g, 0.174 mol) in DMF (300 mL) was added TBSCl (26.01 g, 1.0 eq.) and imidazole (17.7 g, 1.5 eq.). The reaction mixture was stirred at 25° C. for 2 h. The reaction mixture was then partitioned between $H_2O$ (300 mL) and diethyl ether (600 mL). The organic layer was washed by brine (2×300 mL), dried over $MgSO_4$ and purified on $SiO_2$ (5%~30% ethyl acetate/hexane) to yield 4-(tert-butyl-dimethyl-silanyloxymethyl)-2-ethyl-3-methyl-cyclohexanol.

To a solution of oxalyl chloride in DCM (400 mL) at −78° C. was added DMSO (15.6 mL, 3.0 eq.) and the mixture was stirred for 30 min. To the mixture was then added 4-(tert-butyl-dimethyl-silanyloxymethyl)-2-ethyl-3-methyl-cyclohexanol (21.1 g, 73.7 mmol) and the reaction mixture was stirred for 3 h at −78° C. $Et_3N$ (30.7 mL) was added at −78° C. and the mixture warmed to 25° C. over 2 h. The reaction mixture was then diluted with $H_2$ (400 mL). The organic layer was dried over $MgSO_4$ and then concentrated to yield 2-ethyl-3-methyl-4-trimethylsilanyloxymethyl-cyclohexanone.

MS (m/z): 285 (MH$^+$), 283 (MH$^−$).

1-Benzyloxy4-iodo-benzene (5.70 g, 18.37 mmol) was dissolved in anhydrous THF (36 mL) at −10° C. Isopropyl magnesium chloride (1.0 M, 18.37 mL) was added and the mixture was stirred for 3 h. A solution of 2-ethyl-3-methyl-4-trimethylsilanyloxymethyl-cyclohexanone (12.0 g in 50 mL THF) was added slowly over 30 min by syringe pump. The reaction mixture was stirred for 30 min at 25° C. and then refluxed for 30 min. The reaction mixture was then cooled to 25° C., HCl (1.0 N, 80 mL) was added slowly, followed by addition of ethyl acetate (100 mL). The organic layer was washed with $H_2O$ (100 mL), dried over $MgSO_4$ and purified on $SiO_2$ (10~15% ethyl acetate/hexane) to yield 1-(4-benzyloxy-phenyl)-2-ethyl-4-hydroxymethyl-3-methyl-cyclohexanol.

MS (m/z): 469 (MH$^+$), 467 (MH$^−$)

To 1-(4-benzyloxy-phenyl )-2-ethyl-4-hydroxymethyl-3-methyl-cyclohexanol (7.8 g, 0.0166 mol) was added pTSA (1.8 g, 1 eq.) in DCM (100 mL). The reaction mixture was refluxed for 8 h. DCM (200 mL) was added and the mixture was washed with aqueous saturated $NaHCO_3$ (3×300 mL). The organic layer was separated, dried over $MgSO_4$ and purified on $SiO_2$ (50% ethyl acetate/hexane) twice to yield [4-(4-benzyloxy-phenyl)-5-ethyl-6-methyl-cyclohex-3-enyl]-methanol.

MS (m/z): 337 (MH$^+$), 335 (MH$^−$)

To the solution of [4-(4-benzyloxy-phenyl)-5-ethyl-6-methyl-cyclohex-3-enyl]-methanol (3.1 g, 6.8 mmol) in THF (50 mL) was added $BH_3.S(CH_3)_2$ solution (1.0 M in THF, 10.3 mL, 1.5 eq.) at 0° C. The reaction mixture was refluxed for 4 h and then cooled to 0° C. NaOH (20% aqueous, 30 mL) and $H_2O_2$ (50% in $H_2O$, 21 mL) were added at 0° C. The reaction mixture was then stirred at 0~25° C. for 4 h. The reaction mixture was then diluted with ethyl acetate/ $H_2O$ (400 mL/200 mL). The organic layer was separated, dried over $MgSO_4$ and purified on $SiO_2$ (50~100% ethyl acetate/hexane) to yield 2-(4-benzyloxy-phenyl)-3-ethyl-5-hydroxymethyl-4-methyl-cyclohexanol.

MS (m/z): 353 (MH$^+$), 351 (MH$^−$)

To the solution of 2-(4-benzyloxy-phenyl)-3-ethyl-5-hydroxymethyl-4-methyl-cyclohexanol (2.31 g) in DMF (20 mL) was added imidazole (1.17 g, 1.5 eq.) and TBSCl (1.4 g, 1.5 eq.) at 0° C. and the mixture was stirred at 25° C. for 3 h. The reaction mixture was then diluted with water/ether (200/300 mL). The organic layer was washed by brine (3×200) and purified $SiO_2$ (10% ethyl acetate/Hexane) to yield 2-(4-benzyloxy-phenyl)-5-(tert-butyl-dimethyl-silanyloxymethyl)-3-ethyl-4-methyl-cyclohexanol.

MS (m/z): 469 (MH$^+$), 467 (MH$^−$)

To a solution of 2-(4-benzyloxy-phenyl)-5-(tert-butyl-dimethyl-silanyloxymethyl)-3-ethyl-4-methyl-cyclohexanol in DCM (100 mL) was added $NaHCO_3$ (1.0 g) to make a suspension. Dess-Martin periodate (3.2 g ,1.0 eq.) was added at 0° C. The reaction mixture was stirred at 25° C. for 3 h and was then filtered and purified on $SiO_2$ (20% Ethyl acetate/Hexane) to yield 3-ethyl-4-methyl-2-(4-phenoxy-phenyl)-5-trimethylsilanyloxymethyl-cyclohexanone.

MS (m/z): 467, (MH$^+$), 465 (MH$^−$)

To a solution of 3-ethyl-4-methyl-2-(4-phenoxy-phenyl)-5-trimethylsilanyloxymethyl-cyclohexanone (1.8 g, 3.8 mmol) in THF (10 mL) at −10° C. was added Grinard reagent (1.0 M, 7.5 mL). The reaction mixture was stirred at 25° C. for 1 h and then refluxed for 30 min. The reaction mixture was then cooled and diluted with aqueous saturated $NH_4Cl$ (100 mL) and ethyl acetate (100 mL). The organic layer was separated, dried over $MgSO_4$ and purified on $SiO_2$ (100% ethyl acetate) to yield crude product 3-ethyl-1-(4-methoxy-phenyl)-4-methyl-2-(4-phenoxy-phenyl)-5-trimethylsilanyloxymethyl-cyclohexanol. NMR showed S: R product ratio or 2:1. Further purification provide pure 3-ethyl-1-(4-methoxy-phenyl)-4-methyl-2-(4-phenoxy-phenyl)-5-trimethylsilanyloxymethyl-cyclohexanol.

MS (m/z): 575 (MH$^+$), 573 (MH$^−$)

To a solution of 3-ethyl-1-(4-methoxy-phenyl)-4-methyl-2-(4-phenoxy-phenyl)-5-trimethylsilanyloxymethyl-cyclohexanol (400 mg) in $CHCl_3$ (8.0 mL) was added pTSA (400 mg) and the reaction mixture was refluxed for 8 h. The reaction mixture was diluted with $CH_3Cl$ (50 mL) and was washed with aqueous saturated $NaHCO_3$ (10 mL). The organic layer was dried and purified on $SiO_2$ (50% ethyl acetate/hexane) to yield a mixture of 4-[6-ethyl-4-hydroxymethyl-2-(4-methoxy-phenyl)-5-methyl-cyclohex-1-enyl]-phenol and 4-[6-ethyl-4-hydroxymethyl-2-(4-methoxy-phenyl)-5-methyl-cyclohex-2-enyl]-phenol as a very close two spots as determined by TLC.

MS (m/z): 443 (MH$^+$), 441 (MH$^−$).

To the above mixture of 4-[6-ethyl-4-hydroxymethyl-2-(4-methoxy-phenyl)-5-methyl-cyclohex-1-enyl]-phenol and 4-[6-ethyl-4-hydroxymethyl-2-(4-methoxy-phenyl)-5-methyl-cyclohex-2-enyl]-phenol (380 mg) in DCM (10 mL) at −10° C. was added $TiCl_4$ (0.180 mL) and the mixture was stirred for 3 h at −10° C. The reaction mixture was diluted with ethyl acetate/$H_2O$ (200/100 mL). The organic layer was dried and purified on $SiO_2$ to yield two products 4-[6-ethyl-4-hydroxymethyl-2-(4-methoxy-phenyl)-5-methyl-cyclohex-1-enyl]-phenol and 4-[2-ethyl-4-hydroxymethyl-6-(4-methoxy-phenyl)-3-methyl-cyclohexyl]-phenol.

MS (m/z): 353 (MH$^+$), 351 (MH$^−$)

EXAMPLE 5

4-{6-ethyl-4-hydroxymethyl-5-methyl-2-[4-(2-piperidin-1-yl-ethoxy)-phenyl]-cyclohex-1-enyl}-phenol Compound #75

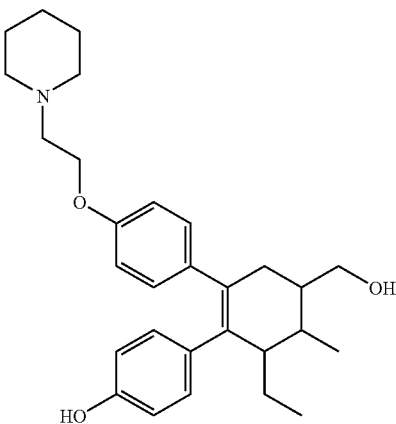

To iodide (66 mg, 0.2 mmol) in THF (1 mL) at −78 C was added nBuLi (2.5 M in hexanes, 0.080 mL, 0.2 mmol) and the reaction mixture stirred for 10 min. To the reaction mixture was then added dropwise, TBS (3-ethyl-4-methyl-2-(4-phenoxy-phenyl)-5-trimethylsilanyloxymethyl-cyclohexanone) in THF (1 mL). The reaction mixture was then quenched with aqueous saturated NH$_4$Cl (2 mL) and diluted with diethyl ether (5 mL). The organic layer was washed with brine twice, dried and concentrated to yield crude 2-(4-benzyloxy-phenyl)-3-ethyl-4-methyl-1-[4-(2-piperidin-1-yl-ethoxy)-phenyl]-5-trimethylsilanyloxy methyl-cyclohexanol which was used without further purification.

MS (m/z): 672 (MH$^+$), 670 (MH$^-$)

To a solution of 2-(4-benzyloxy-phenyl)-3-ethyl-4-methyl-1-[4-(2-piperidin-1-yl-ethoxy)-phenyl]-5-trimethylsilanyloxy methyl-cyclohexanol in DCM (1 mL) was added TiCl$_4$ (0.033 mL, 3 eq.) and the mixture stirred until reaction was done. The reaction mixture was diluted with ethyl acetate (10 mL), and washed with 5% NaHCO$_3$ aqueous solution, then brine. The crude products was purified on HPLC to yield 4-{6-ethyl-4-hydroxymethyl-5-methyl-2-[4-(2-piperidin-1-yl-ethoxy)-phenyl]-cyclohex-1-enyl}-phenol.

MS (m/z): 450 (MH$^+$), 448 (MH$^-$).

EXAMPLE 6

[6-Hydroxymethyl-3,4-bis-(4-methoxy-phenyl)-cyclohex-3-enyl]-methanol Compound #26

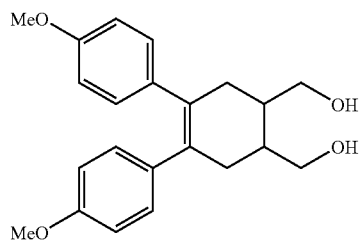

Step 1:
To the solution of 4-methoxy-phenyl-acetylene (10 g, 0.075 mol) and 4-iodo-anisole (17.65 g, 1.0 eq.) in diethylamine (150 mL) was added Pd(PPh$_3$)$_2$Cl$_2$ (2.65 g, 0.05 eq.) and the reaction mixture was stirred for 30 min at 0° C. To the reaction mixture was then added CuI (1.43 g, 0.1 eq.) and the mixture was stirred at 6 h at 0~25° C. The reaction mixture was then concentrated and partitioned between ethyl acetate/H$_2$O (200/600 mL). The organic layer was separated, dried and purified on SiO$_2$ (1~5% ethyl acetate/hexane) to yield 1,2-di(4-methoxy-phenyl)-acetylene.

Step 2:
Sodium hydride (1.53 g, 2.2 eq.) was added to DMSO (150 mL) and then heated to 75° C. till the solution became clear. The reaction mixture was cooled to 0° C. 1,2-di(4-methoxy-phenyl)-acetylene. (7.0 g, 1 eq.) was then added and the reaction mixture was then heated to 90° C. for 12 h. The reaction mixture was then poured into crushed ice and extracted by diethyl ether (500 mL). The organic layer was washed with brine, dried and purified on SiO$_2$ to yield 2,3-di(4-methoxyphenyl)-1,3-butadiene as 80% pure by NMR.

MS (m/z): 267 (MH$^+$), 265 (MH$^-$).

Step 3:
To the solution of 2,3-di(4-methoxyphenyl)-1,3-butadiene (2.1 g) in toluene (30 mL) was added maleic anhydride (3.8 g, 5.0 eq.) and the reaction mixture refluxed for 6 h. The reaction mixture was then diluted with ethyl acetate (500 mL) and was washed with water (3×200 mL). The organic layer was dried and concentrated to yield 5,6-bis-(4-methoxy-phenyl)-3a,4,7,7a-tetrahydro-isobenzofuran-1,3-dione.

MS (m/z): 365 (MH$^+$), 363 (MH$^-$).

Step 4:
To the cooled solution of 5,6-bis-(4-methoxy-phenyl)-3a,4,7,7a-tetrahydro-isobenzofuran-1,3-dione (2.95g) in THF (30 mL) at 0° C. was added LAH (1.0 M in THF, 20 mL) and the reaction mixture was stirred at 25° C. for 16. The reaction mixture was then quenched with methanol (20 mL) and aqueous HCl (10%, 30 mL) and then extracted with diethyl ether (2×300 mL). The organic layer was dried and concentrated to yield [6-Hydroxymethyl-3,4-bis-(4-methoxy-phenyl)-cyclohex-3-enyl]-methanol.

MS (m/z): 355 (MH$^+$), 353 (MH$^-$)

EXAMPLE 7

5,6-Diphenyl-2,3,3a,4,7,7a-hexahydro-inden-1-one Compound #67

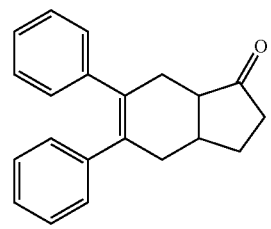

A mixture of 2,3-diphenyl-1,3-butadiene (2.772 g, 13.44 mmol) and cyclopent-2-enone (1 eq.) was refluxed in toluene (26 mL) for 48 h. The reaction mixture was then concentrated and purified on SiO₂ (20% ethyl acetate/hexane) to yield 5,6-diphenyl-2,3,3a,4,7,7a-hexahydro-inden-1-one.

MS (m/z): 289 (MH⁺), 287 (MH⁻).

EXAMPLE 8

5,6-Bis-(4-methoxy-phenyl)-2,3,3a,4,7,7a-hexahydro-1H-inden-1S-ol and 5,6-Bis-(4-methoxy-phenyl)-2,3,3a,4,7,7a-hexahydro-1H-inden-1R-ol Compound #61 and #57

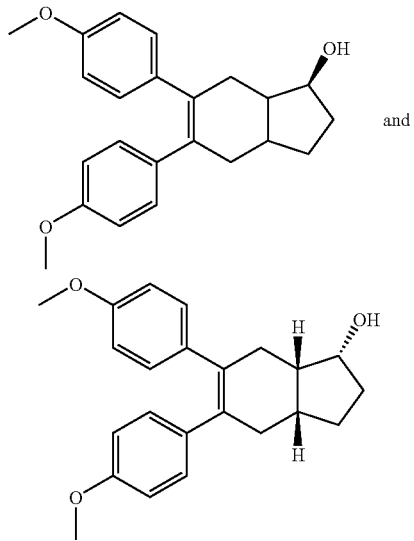

To a solution of 5,6-bis-(4-methoxy-phenyl)-2,3,3a,4,7,7a-hexahydro-inden-1-one (50.0 mg, 0.143 mmol) in THF (5.0 mL) at −10° C. was added LAH (36 mg, 0.91 mml) and the reaction mixture was stirred at −10° C. for 1 h. The reaction mixture was then quenched with methanol (2 mL) and aqueous HCl (1 N, 2 mL), extracted with ethyl acetate (3×10 mL). The combined organic layers were dried and purified on SiO₂ to yield a mixture of 5,6-Bis-(4-methoxy-phenyl)-2,3,3a,4,7,7a-hexahydro-1H-inden-1S-ol and 5,6-Bis-(4-methoxy-phenyl)-2,3,3a,4,7,7a-hexahydro-1H-inden-1R-ol.

MS (m/z): 351 (MH⁺), 349 (MH⁻).

EXAMPLE 9

6,7-Diphenyl-3,4,4a,5,8,8a-hexahydro-2H-naphthalen-1-one Compound #56

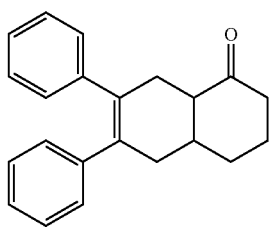

A mixture of 2,3-diphenyl-1,3-butadiene (2.772 g, 13.44 mmol) and cyclohex-2-enone (1 eq.) was refluxed in toluene (26 mL) for 48 h. The reaction mixture was then concentrated and purified on SiO₂ (20% ethyl acetate/hexane) to yield 6,7-diphenyl-3,4,4a,5,8,8a-hexahydro-2H-naphthalen-1-one.

MS (m/z): 303 (MH⁺), 301 (MH⁻).

EXAMPLE 10

6-Hydroxymethyl-3,4-diphenyl-cyclohex-3-enyl)-methanol Compound #34

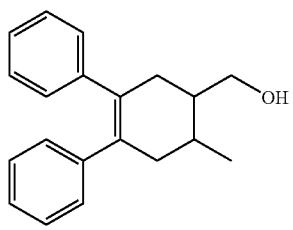

(6-Hydroxymethyl-3,4-diphenyl-cyclohex-3-enyl)-methanol was prepared according to the procedure described in Example 6 (step 3) above, with substitution of 2,3-diphenyl-1,3-butadiene for the 2,3-di(4-methoxyphenyl)-1,3-butadiene.

MS (m/z): 295 (MH⁺), 293 (MH⁻)

To the cooled solution of 6-Hydroxymethyl-3,4-diphenyl-cyclohex-3-enyl)-methanol (100 mg, 0340 mmol) in THF (3.5 mL) at −78° C., was added nBuLi (2.5 M, 0.136 mL). The reaction mixture was stirred at −10° C. for 10 min. To the reaction mixture was added TsCl (77 mg, 1.2 eq.) and the mixture stirred at −10° C. to 25° C. for 3 h. The reaction mixture was quenched with aqueous saturated NaHCO₃ (10 mL) and was extracted with ethyl acetate (3×10 mL). The combined organic layers were dried and purified on SiO₂ (10~50% ethyl acetate/hexane) to yield 6-hydroxymethyl-3,4-diphenyl-cyclohex-3-enyl)-methanol.

MS (m/z): 449 (MH⁺), 447 (MH⁻)

To a solution of 6-hydroxymethyl-3,4-diphenyl-cyclohex-3-enyl)-methanol (89 mg, 0.189 mmol) in THF (10 mL) was added LAH (1.0 M in THF, 5 mL) at ~10° C. (ice/acetone) and the reaction mixture stirred at 25° C. for 12 h. The reaction mixture was then quenched by MeOH (10 mL) and then stirred for 10 min. To the reaction mixture was then added aqueous HCl (10%, 10 mL). The reaction mixture was then extracted with diethyl ether (300 mL). The organic layer was washed with brine, dried and purified to yield 6-hydroxymethyl-3,4-diphenyl-cyclohex-3-enyl)-methanol and 5,6-diphenyl-1,3,3a,4,7,7a-hexahydro-isobenzofuran as a by product.

MS (m/z): 277 (MH⁺), 275 (MH⁻).

EXAMPLE 11

4-{4-Hydroxymethyl-5-methyl-6-[4-(2-piperidin-1-yl-ethoxy)-benzyl]-cyclohexa-1,5-dienyl}-S-phenol Compound #74

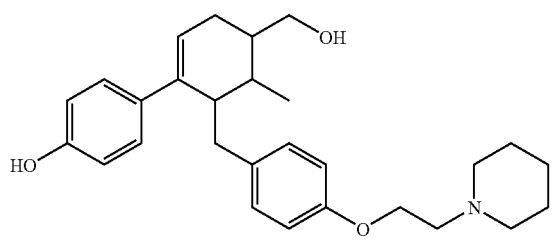

Step 1:

To the solution of KOtBu (1.0 M in tBuOH, 10.7 mL) at 25 cC was added Hagemann's ester (1.0 mL, 5.324 mmol). The mixture was stirred for 10 min at 25° C. and then to the mixture was added 1-[2-(4-chloromethyl-phenoxy)ethyl]piperidine hydrochloride (1.54 g, 5.324 mmol). The mixture was refluxed for 3 h. The tBuOH was distilled off, then the reaction mixture was diluted with water and diethyl ether. The layers were separated and the aqueous layer was extracted with diethyl ether. The organic extracts were acidified with 1N HCl (100 mL). The layers were separated and the diethyl ether layer was discarded. The aqueous layer was then basicified to pH 11 with 10% NaOH (aq) and extracted with diethyl ether to yield 2-methyl-4-oxo-3-[4-(2-piperidin-1-yl-ethoxy)-benzyl]-cyclohex-2-enecarboxylic acid ethyl ester as dark amber oil.

MS (m/z): 400 (MH$^+$).

Step 2:

A solution of 2-methyl-4-oxo-3-[4-(2-piperidin-1-yl-ethoxy)-benzyl]-cyclohex-2-enecarboxylic acid ethyl ester (612.0 mg, 1.534 mmol) in EtOH (100 mL) was reacted with 10% Pd/C (25 mg) under H$_2$(g) (25 psi) for 21 h at 25° C. The reaction mixture was then filtered and concentrated to yield 4-ethylperoxymethyl-3-methyl-2-[4-(2-piperidin-1-yl-ethoxy)-benzyl]-cycloxe-2-enone.

MS (m/z): 402 (MH$^+$).

Step 3:

To a solution of KHMDS (0.5 M in toluene), 5.9 mL) in THF (20 mL) at −78° C. was added 4-ethylperoxymethyl-3-methyl-2-[4-(2-piperidin-1-yl-ethoxy)-benzyl ]-cycloxe-2-enone (0.985 mg, 2.453 mmol) in THF (3 mL) and the reaction mixture stirred at −78° C. for 1 h. To the reaction mixture was then added 2-[N,N-bis(trifluoro-methyl-sulfonyl)amino]-5-chloropyridine in THF (2 mL) and the mixture was stirred at −78° C. for 1.5 h. The reaction mixture was then quenched with water, extracted with Et$_2$O, dried and purified on silica gel (2% MeOH/CH$_2$Cl$_2$) followed by a preparative TLC (5% MeOH/DCM) to yield 6-methyl-5-[4-(2-piperidiny-1-yl-ethoxy)-benzyl]-4-trifluoromethane-sulfonyloxy-cyclohex-3-enecarboxylic acid ethyl ester as white foam solid.

MS (m/z): 534 (MH$^+$).

Step 4:

Into a mixture of trifluoro-methanesulfonic acid 4-ethylperoxymethyl-5-methyl-6-[4-(2-piperidin-1-yl-ethoxy)-benzyl]-cyclohexa-1,5-dienyl ester (118.5 mg, 0.2219 mmol), Pd (PPh$_3$)$_4$ (6.4 mg, 0.025 eq.) and K$_3$PO$_4$ (70.7 mg, 1.5 eq.) in 1,4-dioxane (5 mL) was bubbled N$_2$ for 10 min. To the reaction mixture was then added 4-methoxy benzene boronic acid (37.1 mg, 0.2441 mmol). The resulting mixture was heated to 8° C. for 16 h, filtered through a plug of silica gel, concentrated and purified on preparative TLC (10% MeOH/DCM) to yield 4-(4-methoxy-phenyl)-6-methyl-5-[4-(2-piperidin-1-yl-ethoxy)-benzyl]-cyclohex-3-enecarboxylic acid ethyl ester as light yellow oil.

MS (m/z): 492 (MH$^+$).

4-{4-Ethylperoxymethyl-5-methyl-6-[4-(2-piperidin-1-yl-ethoxy)-benzyl]-cyclohexa-1,5-dienyl}-phenol was similarly prepared according to the procedure described above with substitution of 4-hydroxy benzene boronic acid for the 4-methoxy benzene boronic acid in Step 4.

MS (m/z): 478 (MH$^+$).

1-(2-{4-[3-Ethylperoxymethyl-6-(4-fluoro-phenyl )-2-methyl-cyclohexa-1,5-dienylmethyl]-phenoxy}-ethyl)-piperidine was similarly prepared according to the procedure described above with substitution of 4-fluorobenzene boronic acid for the 4-methoxy benzene boronic acid in Step 4.

MS (m/z): 480 (MH$^+$).

5-(4-{4-Ethylperoxymethyl-5-methyl-6-[4-(2-piperidin-1-yl-ethoxy)-benzyl]-cyclohexa-1,5-dienyl}-phenyl)-1H-indole was similarly prepared according to the procedure described above with substitution of 5-indolyl boronic acid for the 4-methoxy benzene boronic acid in Step 4.

MS (m/z): 501 (MH$^+$).

Step 5:

4-(4-Hydroxy-phenyl)-6-methyl-5-[4-(2-piperidin-1-yl-ethoxy)-benzyl]-cyclohex-3-enecarboxylic acid ethyl ester (38.4 mg, 0.0803 mmol, 1.0 eq.) in DCM (2 mL) at 0° C. was added DIBAL (1.5 M in toluene, 0.215 mL) and was stirred at 0° C. for 10 min, then at 25° C. for 30 min. The reaction mixture was quenched at 0° C. with brine, extracted with DCM, dried over MgSO$_4$, then purified on SiO$_2$ (15% MeOH/DCM) to yield 4-[4-hydroxymethyl-5-methyl-6-[4-(2-piperidin-1-yl-ethoxy)-benzyl]-cyclohex-3-enyl]-phenol as yellowish foam.

MS (m/z): 436 (MH$^+$).

EXAMPLE 12

Estrogen Receptor α Flash Plate Assay

This assay monitors binding of radio-labeled estrogen to the estrogen receptor. It is performed on a BioMek 2000 (Beckman). Plates are read in a scintillation counter (Packard TopCount), with decreased counts an indication of binding of a compound to the receptor. The assay was run according to the procedure described by Allan, et al., *Anal. Biochem.* (1999), 275(2), 243–247.

On day one, 100 μL of Estrogen Screening Buffer (ESB, Panvera) containing 5 mM dithiothreitol (DTT, Panvera), 0.5 μg mouse anti-estrogen receptor monoclonal antibody (SRA-1010, Stressgen) and 50 ng purified human estrogen receptor α (Panvera) were added to each well of a 96 well FlashPlate Plus plate crosslinked with goat anti-mouse antibodies (NEN Life Sciences). The plate was sealed and incubated at 4° C. overnight.

On day two, each well was washed three times with 200 μL PBS, pH 7.2, at room temperature. To each well was then added 98 μL radio-labeled estrogen (0.5 nM, which equals 6 nCi for a 120 Ci/mmol batch, Amersham), diluted in ESB and 5 mM dithiothreitol (DTT). To individual wells were then added 2.5 µL test compound diluted in 30% (v/v) dimethyl sulfoxide/50 mM HEPES, pH 7.5. The wells were mixed three times by aspiration, the plate sealed and incubated at room temperature for one hour. The wells were then counted for 1 min in a TopCount scintillation counter (Packard).

EXAMPLE 13

Estrogen Receptor β Fluorescence Polarization Assay

This assay monitors binding of a fluorescent analog of estrogen (Fluormone ES2, Panvera) to the estrogen receptor. Plates are read in a fluorometer that can be set to polarization mode. A decrease in fluorescence relative to vehicle control is an indication of binding of a compound to the receptor.

It is crucial to avoid introduction of air bubbles into the reaction in each well of the 96 well plate throughout this procedure. (Bubbles on the surface of the reaction disrupt light flow, affecting the polarization reading.) However, it is also crucial to effectively mix the reaction components upon addition to the well.

On ice, a 2× standard mixture of Assay Buffer (Panvera), 10 nM DTT and 40 nM ES2 was prepared. On ice, a 2× reaction mixture of Assay Buffer (Panvera), and 20 nM hER-β (Panvera) and 40 nM ES2 was also prepared.

Dilutions of test compound were prepared in 30% (v/v) dimethyl sulfoxide/50 mM HEPES, pH 7.5. At this point, the dilutions were 40× the final required concentration.

The standard mixture at 50 µL was then added to each well. The reaction mixture at 48 µL was added to all wells. The compound dilution at 2.5 µL was added to the appropriate wells. The reaction mixtures were mixed using a manual pipette, a roll of aluminum foil adhesive cover was placed on the plate and the plate incubated at room temperature for 1 hour.

Each well on the plate was then read in an LjL Analyst with an excitation wavelength of 265 nm and an emission wavelength of 538.

Representative compound of the present invention were tested according to the procedure described above for binding to the Estrogen Receptor α and Estrogen Receptor β, with results as listed in Table 6.

TABLE 6

| ID No. | ERα Binding IC$_{50}$ (µM) | ERβ Binding IC$_{50}$ (µM) |
|---|---|---|
| 3 | 6.1 | 5.7 |
| 4 | >10 | 1.6 |
| 18 | >10 | <10 |
| 20 | 1.85 | 0.10 |
| 25 | 0.45 | 0.35 |
| 26 | >10 | >10 |
| 27 | 0.5 | 1.5 |
| 36 | >10 | 6.9 |
| 38 | 0.037, 0.01 | 0.9, 0.5 |
| 39 | >10 | >10 |
| 43 | 0.045 | >10, 8 |
| 45 | 4.5 | >10 |
| 46 | 0.2 | 0.74 |
| 52 | >10 | 5.7 |
| 57 | >10 | 4.9 |
| 61 | 8.7 | 2.0 |
| 74 | 0.37 | 0.38 |

EXAMPLE 14

MCF-7 Cell Proliferation Assay

This assay was run according to the procedure described by Welshons, et al., (*Breast Cancer Res. Treat.*, 1987, 10(2), 169–75), with minor modification.

Briefly, MCF-7 cells (from Dr. C. Jordan, Northwestern University) were maintained in RPMI 1640 phenol red free medium (Gibco) in 10% FBS (Hyclone), supplemented with bovine insulin and non-essential amino acid (Sigma). The cells were initially treated with 4-hydroxytamoxifen ($10^{-8}$ M) and let stand at 37° C. for 24 hours. Following this incubation with tamoxifen, the cells were treated with compounds at various concentrations.

Compounds to be tested in the agonist mode were added to the culture media at varying concentrations. Compounds to be treated in the antagonist mode were prepared similarly, and 10 nM 17β-estradiol was also added to the culture media. The cells were incubated for 24 hours at 37° C. Following this incubation, 0.1 µCi of $^{14}$C-thymidine (56mCi/mmol, Amersham) was added to the culture media and the cells were incubated for an additional 24 hours at 37° C. The cells were then washed twice with Hank's buffered salt solution (HBSS) (Gibco) and counted with a scintillation counter. The increase in the $^{14}$C-thymidine in the compound treated cells relative to the vehicle control cells were reported as percent increase in cell proliferation.

EXAMPLE 15

Alkaline Phosphatase Assay in Human Endometrial Ishikawa Cells

This assay was run according to the procedure described by Albert et a., *Cancer Res*, (9910), 50(11), 330-6-10, with minor modification.

Ishikawa cells (from ATCC) were maintained in DMEM/F12 (1:1) phenol red free medium (Gibco) supplemented with 10% calf serum (Hyclone). 24 hours prior to testing, the medium was changed to DMEM/F12 (1:1) phenol red free containing 2% calf serum.

Compounds to be tested in the agonist mode were added to the culture media at varying concentrations. Compounds to be treated in the antagonist mode were prepared similarly, and 10 nM 17β-estradiol was also added to the culture media. The cells were then incubated at 37° C. for 3 days. On the fourth day, the media was remove, 1 volume of 1× Dilution Buffer (Clontech) was added to the well followed by addition of 1 volume of Assay Buffer (Clontech). The cells were then incubated at room temperature for 5 minutes. 1 volume of freshly prepared Chemiluminescence Buffer (1 volume of chemiluminescent substrate (CSPD) in 19 volume Chemiluminescent Enhancer with final concentration of CSPD at 1.25 mM; Sigma Chemical Co.) was added. The cells were incubated at room temperature for 10 minutes and then quantified on a luminometer. The increase of chemiluminescence over vehicle control was used to calculate the increase in alkaline phosphatase activity.

Representative compound of the present invention were tested according to the procedure described in Examples 14 and 15 above, with results as listed in Table. 7.

TABLE 7

| ID No. | MCF7 Agonist EC$_{50}$ (nM) | MCF7 Antagonist IC$_{50}$ (nM) | Ishikawa Agonist EC$_{50}$ (nM) | Ishikawa Antagonist IC$_{50}$ (nM) |
|---|---|---|---|---|
| 4 | >10,000 | >10,000 | >10,000 | >10,000 |
| 18 | >10,000 | >10,000 | >10,000 | >10,000 |
| 20 | 480 | >10,000 | 700 | 4,500 |
| 25 | 200 | >10,000 | 100 | 10,000 |
| 26 | >10,000 | >10,000 | >10,000 | >10,000 |
| 27 | >10,000 | >10,000 | >10,000 | >10,000 |
| 38 | >10,000 | 5000 | >10,000 | 2100 |
| 39 | >10,000 | >10,000 | >10,000 | >10,000 |
| 43 | >10,000 | 5000 | >10,000 | 2700 |
| 45 | >10,000 | >10,000 | >10,000 | 7000 |
| 46 | >10,000 | >10,000 | >10,000 | >10,000 |
| 52 | >10,000 | >10,000 | >10,000 | >10,000 |
| 56 | >10,000 | >10,000 | >10,000 | >10,000 |
| 61 | >10,000 | >10,000 | >10,000 | >10,000 |

EXAMPLE 16

As a specific embodiment of an oral composition, 100 mg of the Compouind #43, is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variation, adaptations and/or modifications as come within the scope of the following claims and their equivalents.

What is claimed is:

1. A compound of formula (II)

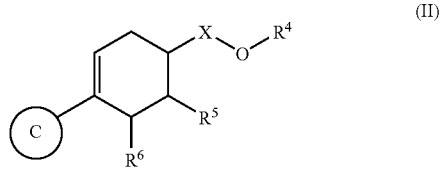

(II)

wherein

X is selected from the group consisting C(O) and CH$_2$;

R$^4$ is selected from the group consisting of hydrogen and lower alkyl;

R$^5$ is selected from the group consisting of alkyl;

R$^6$ is selected from the group consisting of -(aralkyl)-Q-(alkyl)-NR$^A$R$^b$;

Q is selected from the group consisting of O and S;

R$^A$ and R$^B$ are each independently selected from the group consisting of hydrogen and alkyl; alternatively R$^A$ and R$^B$ are taken together with the N atom to which they are bound to form a heteroaryl or heterocycloalkyl group;

Ⓒ is selected from the group consisting of phenyl optionally substituted with one or more substitutents independently selected from halogen, hydroxy, alkoxy, aralkyloxy or NR$^A$R$^B$-alkoxy;

or a pharmaceutically acceptable salt thereof.

2. A compound as in claim 1 wherein

X is selected from the group consisting C(O) and CH$_2$;

R$^4$ is selected from the group consisting of hydrogen and lower alkyl;

R$^5$ is selected from the group consisting of lower alkyl;

R$^6$ is selected from the group consisting of -(benzyl)-Q-(lower alkyl)-NR$^A$R$^B$;

Q is selected from the group consisting of O and S;

R$^A$ and R$^B$ are each independently selected from the group consisting of hydrogen and lower alkyl; alternatively R$^A$ and R$^B$ are taken together with the N atom to which they are bound to form a five to six membered heteroaryl or a five to six membered heterocycloalkyl group;

Ⓒ is selected from the group consisting of phenyl optionally substituted with one to two substitutents independently selected from halogen, hydroxy, alkoxy, aralkyloxy or NR$^A$ R$^B$ -alkoxy;

or a pharmaceutically acceptable salt thereof.

3. A compound as in claim 2 wherein

X is C(O);

R$^4$ is selected from the group consisting of lower alkyl;

R$^5$ is selected from the group consisting of lower alkyl;

R$^6$ is selected from the group consisting of(benzyl)-O-(lower alkyl)-NR$^A$ R$^B$;

wherein R$^A$ and R$^B$ are each independently selected from lower alkyl; alternatively R$^A$ and R$^B$ are taken together with the N atom to which they are bound to form a five to six membered heteroaryl or five to six membered heterocycloalkyl group;

Ⓒ is selected from the group consisting of phenyl optionally substituted with a substituent selected from halogen, hydroxy or lower alkoxy;

or a pharmaceutically acceptable salt thereof.

4. A compound as in claim 3 wherein

X is C(O);

Ⓒ is selected from the group consisting of 4-fluorophenyl, and 4-hydroxyphenyl;

R$^4$ is ethyl;

R$^5$ is methyl;

R$^6$ is selected from the group consisting of 4-(dimethylamino-ethoxy)-benzyl, 4-(morpholinyl-ethoxy)-benzyl, 4-(piperidinyl-ethoxy)-benzyl and 4-(pyrrolidinyl-ethoxy)-benzyl;

or a pharmaceutically acceptable salt thereof.

* * * * *